US012712074B2

(12) United States Patent
Tiron et al.

(10) Patent No.: US 12,712,074 B2
(45) Date of Patent: Aug. 18, 2026

(54) SYSTEMS AND METHODS FOR MONITORING A COMFORT LEVEL OF AN INDIVIDUAL

(71) Applicant: ResMed Sensor Technologies Limited, Dublin (IE)

(72) Inventors: Roxana Tiron, Dublin (IE); Michael Scannell, Dublin (IE); Kieran Conway, Dublin (IE); Redmond Shouldice, Dublin (IE)

(73) Assignee: ResMed Sensor Technologies Limited, Dublin (IE)

( * ) Notice: Subject to any disclaimer, the term of this patent is extended or adjusted under 35 U.S.C. 154(b) by 490 days.

(21) Appl. No.: 18/037,126

(22) PCT Filed: Nov. 19, 2021

(86) PCT No.: PCT/IB2021/060763
§ 371 (c)(1),
(2) Date: May 16, 2023

(87) PCT Pub. No.: WO2022/107075
PCT Pub. Date: May 27, 2022

(65) Prior Publication Data

US 2023/0420124 A1 Dec. 28, 2023

Related U.S. Application Data

(60) Provisional application No. 63/116,760, filed on Nov. 20, 2020.

(51) Int. Cl.

| | |
|---|---|
| ***G16H 40/63*** | (2018.01) |
| ***A61B 5/00*** | (2006.01) |
| ***G16H 10/60*** | (2018.01) |

(52) U.S. Cl.
CPC ........... *G16H 40/63* (2018.01); *A61B 5/4809* (2013.01); *G16H 10/60* (2018.01)

(58) Field of Classification Search
CPC ........ G16H 40/63; G16H 40/67; G16H 10/60; G16H 50/20; G16H 50/30; A61B 5/4809
See application file for complete search history.

(56) References Cited

U.S. PATENT DOCUMENTS 9,358,353 B2 6/2016 Armitstead et al.
10,424,401 B2 * 9/2019 Harris .................... G16H 10/20
(Continued)

FOREIGN PATENT DOCUMENTS

WO 2008/138040 A1 11/2008
WO 2012/012835 A2 2/2012
(Continued)

OTHER PUBLICATIONS

International Search Report in International Patent Application No. PCT/IB2021/060763 mailed Feb. 24, 2022 (3 pp.).
(Continued)

*Primary Examiner* — Mong-Shune Chung
(74) *Attorney, Agent, or Firm* — Nixon Peabody LLP

(57) ABSTRACT

A method includes generating, using one or more sensors, data. The data includes (i) environmental data related to an environment of a user and (ii) physiological data associated with the user during a sleep session. Based at least in part on the physiological data, a comfort score associated with the user during the sleep session is determined. The comfort score is indicative of a comfort level of the user during at least a portion of the sleep session. Based at least in part on the determined comfort score, a setting of one or more devices associated with the environment of the user is adjusted.

20 Claims, 5 Drawing Sheets

(56) References Cited

U.S. PATENT DOCUMENTS

| | | | | |
|---|---|---|---|---|
| 11,004,322 | B2 * | 5/2021 | Pekarske | A61B 5/0816 |
| 2002/0014951 | A1 * | 2/2002 | Kramer | G16H 10/60 340/286.07 |
| 2014/0088373 | A1 | 3/2014 | Phillips et al. | |
| 2017/0095670 | A1 * | 4/2017 | Ghaffari | A61M 21/02 |
| 2018/0106897 | A1 | 4/2018 | Shouldice et al. | |
| 2019/0095957 | A1 * | 3/2019 | Ibarria | G16H 10/20 |
| 2021/0241125 | A1 * | 8/2021 | Jost | G06N 20/10 |

FOREIGN PATENT DOCUMENTS

| | | | | |
|---|---|---|---|---|
| WO | 2014/047310 | A1 | 3/2014 | |
| WO | 2015/054134 | A1 | 4/2015 | |
| WO | 2016/061629 | A1 | 4/2016 | |
| WO | 2017/132726 | A1 | 8/2017 | |
| WO | 2018/050913 | A1 | 3/2018 | |
| WO | 2019/122413 | A1 | 6/2019 | |
| WO | WO-2019122414 | A1 * | 6/2019 | G01C 21/3407 |
| WO | 2020/104465 | A2 | 5/2020 | |
| WO | 2021/152526 | A1 | 8/2021 | |

OTHER PUBLICATIONS

Written Opinion in International Patent Application No. PCT/IB2021/060763 mailed Feb. 24, 2022 (8 pp.).

* cited by examiner

SYSTEMS AND METHODS FOR MONITORING A COMFORT LEVEL OF AN INDIVIDUAL

CROSS-REFERENCE TO RELATED APPLICATIONS

This application is a U.S. National Stage of International Application No. PCT/IB2021/060763, filed Nov. 19, 2021, which claims the benefit of and priority to U.S. Provisional Patent Application No. 63/116,760, filed Nov. 20, 2020, which is hereby incorporated by reference herein in its entirety.

TECHNICAL FIELD

The present disclosure relates generally to systems and methods for improving a physical comfort level of an individual in an environment, and more particularly, to systems and methods for changing an individual's environment using one or more devices such that the individual's comfort level is improved or maintained over time.

BACKGROUND

Many individuals suffer from sleep-related and/or respiratory disorders such as, for example, Periodic Limb Movement Disorder (PLMD), Restless Leg Syndrome (RLS), Sleep-Disordered Breathing (SDB) such as Obstructive Sleep Apnea (OSA), Central Sleep Apnea (CSA), other types of apneas such as mixed apneas and hypopneas, Respiratory Effort Related Arousal (RERA), Cheyne-Stokes Respiration (CSR), respiratory insufficiency, Obesity Hyperventilation Syndrome (OHS), Chronic Obstructive Pulmonary Disease (COPD), Neuromuscular Disease (NMD), chest wall disorders, and insomnia. Many of these disorders can be treated using a respiratory therapy system, while others may be treated using a different technique(s) and/or medicaments. However, some users find such respiratory therapy systems to be uncomfortable, difficult to use, expensive, aesthetically unappealing and/or fail to perceive the benefits associated with using the system. As a result, some users may elect not to use the respiratory therapy system diligently, in particular absent a demonstration of the severity of their symptoms when the respiratory therapy treatment is not used. Improving a user's wellbeing and physical comfort can help improve diligence. The present disclosure is directed to solving these and other problems.

SUMMARY

According to some implementations of the present disclosure, a method includes generating, using one or more sensors, data. The data includes (i) environmental data related to an environment of a user and (ii) physiological data associated with the user during a sleep session. Based at least in part on the physiological data, a comfort score associated with the user during the sleep session is determined. The comfort score is indicative of a comfort level of the user during at least a portion of the sleep session. Based at least in part on the determined comfort score, a setting of one or more devices associated with the environment of the user is adjusted.

According to some implementations of the present disclosure, a method includes generating environmental data related to an environment of a user. The environmental data is analyzed to determine a relationship between one or more environmental parameters within the environmental data and a comfort score of the user. The one or more environmental parameters is controlled by one or more devices. One or more settings of the one or more devices is adjusted, based on the relationship, to improve the comfort score of the user.

According to some implementations of the present disclosure, a system for improving or maintaining a comfort level of a user is provided. The system includes a sensor configured to generate first data. The first data includes (i) first environmental data related to an environment of a user and (ii) first physiological data associated with the user during a sleep session. The system further includes one or more devices associated with the environment of the user, a memory storing machine-readable instructions, and a control system including one or more processors configured to execute the machine-readable instructions to: based at least in part on the first physiological data, determine a comfort score associated with the user during the sleep session, the comfort score being indicative of a comfort level of the user during at least a portion of the sleep session; and based at least in part on the determined comfort score, adjust a setting of the one or more devices associated with the environment of the user.

The above summary is not intended to represent each implementation or every aspect of the present disclosure. Additional features and benefits of the present disclosure are apparent from the detailed description and figures set forth below.

Figure 1:
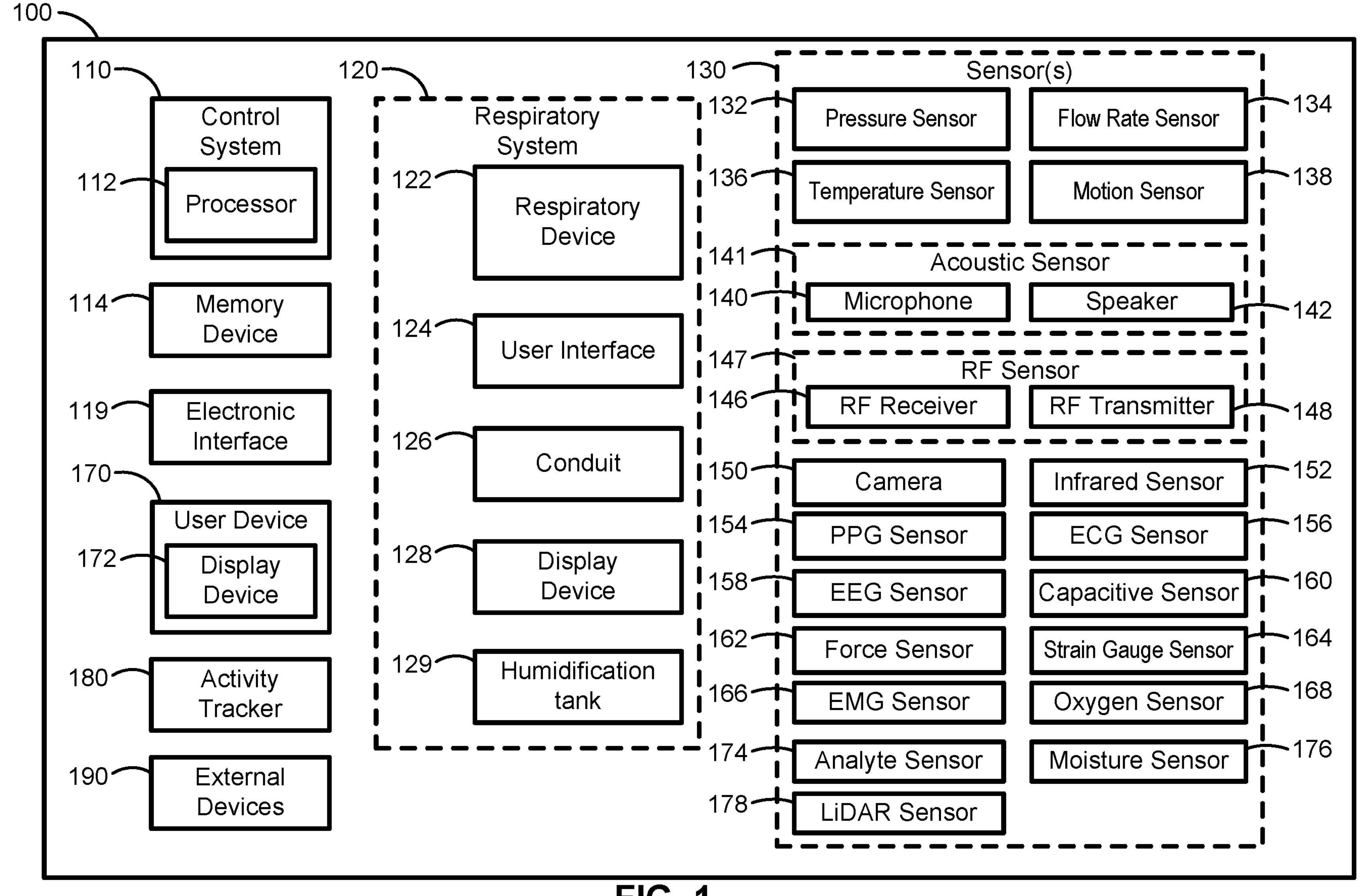
FIG. 1 is a functional block diagram of a system, according to some implementations of the present disclosure.

While the present disclosure is susceptible to various modifications and alternative forms, specific implementations and embodiments thereof have been shown by way of example in the drawings and will herein be described in detail. It should be understood, however, that it is not intended to limit the present disclosure to the particular forms disclosed, but on the contrary, the present disclosure is to cover all modifications, equivalents, and alternatives falling within the spirit and scope of the present disclosure as defined by the appended claims.

DETAILED DESCRIPTION

Many individuals seek to be comfortable in their environment. Comfort is a subjective feeling which can influence an individual's focus, happiness, energy, alertness, stress, etc. Due to the subjective nature of comfort, choices and environmental conditions that influence comfort also change over time. For example, an individual that enjoys a black morning coffee can one day develop a taste for cream in her coffee. Once that taste is developed, the individual can become more comfortable and/or prefer cream in her coffee over black morning coffee. Thus, introducing the individual to new items in an environment or introducing the individual to new environmental conditions can adjust the individual's preferences. Although preferences can be in flux, newly developed preferences may not be readily apparent to the individual.

Subjective feelings can have objective signatures. For example, an individual may be uncomfortable in a room with a temperature of about 24° C. (~75° F.). The individual can perspire more than usual under this temperature. The individual can experience heavy breathing. In some cases, the individual's blood oxygen level can slightly decrease. These individual's bodily responses to the room's temperature can be observed to determine whether the individual is comfortable.

There is also a nexus between diseases or disorders, comfort, and therapies that address the diseases or disorders. Diseases and disorders can make an individual uncomfortable, and therapies can be used for treatment. Sometimes, the therapies themselves are also uncomfortable, even more so than the perceived discomfort of the disease. The present disclosure provides systems and methods for improving comfort in general, and also for improving comfort in the context of sleep-related and/or respiratory disorders. Sleep-related and/or respiratory disorders are merely provided as examples. The present disclosure can be combined to improve comfort in other situations. Many individuals suffer from sleep-related and/or respiratory disorders. Examples of sleep-related and/or respiratory disorders include Periodic Limb Movement Disorder (PLMD), Restless Leg Syndrome (RLS), Sleep-Disordered Breathing (SDB) such as Obstructive Sleep Apnea (OSA), Central Sleep Apnea (CSA), and other types of apneas such as mixed apneas and hypopneas, Respiratory Effort Related Arousal (RERA), Cheyne-Stokes Respiration (CSR), respiratory insufficiency, Obesity Hyperventilation Syndrome (OHS), Chronic Obstructive Pulmonary Disease (COPD), Neuromuscular Disease (NMD), rapid eye movement (REM) behavior disorder (also referred to as RBD), dream enactment behavior (DEB), hypertension, diabetes, stroke, insomnia, and chest wall disorders.

Obstructive Sleep Apnea (OSA) is a form of Sleep Disordered Breathing (SDB), and is characterized by events including occlusion or obstruction of the upper air passage during sleep resulting from a combination of an abnormally small upper airway and the normal loss of muscle tone in the region of the tongue, soft palate and posterior oropharyngeal wall. More generally, an apnea generally refers to the cessation of breathing caused by blockage of the air (Obstructive Sleep Apnea) or the stopping of the breathing function (often referred to as Central Sleep Apnea). Typically, the individual will stop breathing for between about 15 seconds and about 30 seconds during an obstructive sleep apnea event.

Other types of apneas include hypopnea, hyperpnea, and hypercapnia. Hypopnea is generally characterized by slow or shallow breathing caused by a narrowed airway, as opposed to a blocked airway. Hyperpnea is generally characterized by an increase depth and/or rate of breathing. Hypercapnia is generally characterized by elevated or excessive carbon dioxide in the bloodstream, typically caused by inadequate respiration.

Cheyne-Stokes Respiration (CSR) is another form of sleep disordered breathing. CSR is a disorder of a patient's respiratory controller in which there are rhythmic alternating periods of waxing and waning ventilation known as CSR cycles. CSR is characterized by repetitive de-oxygenation and re-oxygenation of the arterial blood.

Obesity Hyperventilation Syndrome (OHS) is defined as the combination of severe obesity and awake chronic hypercapnia, in the absence of other known causes for hypoventilation. Symptoms include dyspnea, morning headache and excessive daytime sleepiness.

Chronic Obstructive Pulmonary Disease (COPD) encompasses any of a group of lower airway diseases that have certain characteristics in common, such as increased resistance to air movement, extended expiratory phase of respiration, and loss of the normal elasticity of the lung.

Neuromuscular Disease (NMD) encompasses many diseases and ailments that impair the functioning of the muscles either directly via intrinsic muscle pathology, or indirectly via nerve pathology. Chest wall disorders are a group of thoracic deformities that result in inefficient coupling between the respiratory muscles and the thoracic cage.

A Respiratory Effort Related Arousal (RERA) event is typically characterized by an increased respiratory effort for ten seconds or longer leading to arousal from sleep and which does not fulfill the criteria for an apnea or hypopnea event. RERAs are defined as a sequence of breaths characterized by increasing respiratory effort leading to an arousal from sleep, but which does not meet criteria for an apnea or hypopnea. These events must fulfil both of the following criteria: (1) a pattern of progressively more negative esophageal pressure, terminated by a sudden change in pressure to a less negative level and an arousal, and (2) the event lasts ten seconds or longer. In some implementations, a Nasal Cannula/Pressure Transducer System is adequate and reliable in the detection of RERAs. A RERA detector may be based on a real flow signal derived from a respiratory therapy device. For example, a flow limitation measure may be determined based on a flow signal. A measure of arousal may then be derived as a function of the flow limitation measure and a measure of sudden increase in ventilation. One such method is described in WO 2008/138040 and U.S. Pat. No. 9,358,353, assigned to ResMed Ltd., the disclosure of each of which is hereby incorporated by reference herein in their entireties.

These and other disorders are characterized by particular events (e.g., snoring, an apnea, a hypopnea, a restless leg, a sleeping disorder, choking, an increased heart rate, labored breathing, an asthma attack, an epileptic episode, a seizure, or any combination thereof) that can occur when the individual is sleeping.

The Apnea-Hypopnea Index (AHI) is an index used to indicate the severity of sleep apnea during a sleep session. The AHI is calculated by dividing the number of apnea and/or hypopnea events experienced by the user during the sleep session by the total number of hours of sleep in the sleep session. The event can be, for example, a pause in breathing that lasts for at least 10 seconds. An AHI that is less than 5 is considered normal. An AHI that is greater than or equal to 5, but less than 15 is considered indicative of mild sleep apnea. An AHI that is greater than or equal to 15, but less than 30 is considered indicative of moderate sleep apnea. An AHI that is greater than or equal to 30 is considered indicative of severe sleep apnea. In children, an AHI that is greater than 1 is considered abnormal. Sleep apnea can be considered "controlled" when the AHI is normal, or when the AHI is normal or mild. The AHI can also be used in combination with oxygen desaturation levels to indicate the severity of Obstructive Sleep Apnea. The AHI calculated based on apnea and/or hypopnea events experienced by the user during the sleep session and while on respiratory therapy is known as "residual" AHI.

Referring to FIG. 1, a system 100, according to some implementations of the present disclosure, is illustrated. The system 100 includes a control system 110, a memory device 114, an electronic interface 119, one or more sensors 130, and one or more user devices 170. In some implementations, the system 100 further optionally includes a respiratory therapy system 120, an activity tracker 180, or any combination thereof.

The control system 110 includes one or more processors 112 (hereinafter, processor 112). The control system 110 is generally used to control (e.g., actuate) the various components of the system 100 and/or analyze data obtained and/or generated by the components of the system 100. The processor 112 can be a general or special purpose processor or microprocessor. While one processor 112 is shown in FIG. 1, the control system 110 can include any suitable number of processors (e.g., one processor, two processors, five processors, ten processors, etc.) that can be in a single housing, or located remotely from each other. The control system 110 can be coupled to and/or positioned within, for example, a housing of the user device 170, a portion (e.g., a housing) of the respiratory therapy system 120, and/or within a housing of one or more of the sensors 130. The control system 110 can be centralized (within one such housing) or decentralized (within two or more of such housings, which are physically distinct). In such implementations including two or more housings containing the control system 110, such housings can be located proximately and/or remotely from each other.

The memory device 114 stores machine-readable instructions that are executable by the processor 112 of the control system 110. The memory device 114 can be any suitable computer readable storage device or media, such as, for example, a random or serial access memory device, a hard drive, a solid state drive, a flash memory device, etc. While one memory device 114 is shown in FIG. 1, the system 100 can include any suitable number of memory devices 114 (e.g., one memory device, two memory devices, five memory devices, ten memory devices, etc.). The memory device 114 can be coupled to and/or positioned within a housing of the respiratory therapy device 122, within a housing of the user device 170, the activity tracker 180, within a housing of one or more of the sensors 130, or any combination thereof. Like the control system 110, the memory device 114 can be centralized (within one such housing) or decentralized (within two or more of such housings, which are physically distinct).

In some implementations, the memory device 114 (FIG. 1) stores a user profile associated with the user. The user profile can include, for example, demographic information associated with the user, biometric information associated with the user, medical information associated with the user, self-reported user feedback, sleep parameters associated with the user (e.g., sleep-related parameters recorded from one or more earlier sleep sessions), or any combination thereof. The demographic information can include, for example, information indicative of an age of the user, a gender of the user, a race of the user, an ethnicity of the user, a geographic location of the user, a travel history of the user, a relationship status, a status of whether the user has one or more pets, a status of whether the user has a family, a family history of insomnia, an employment status of the user, an educational status of the user, a socioeconomic status of the user, or any combination thereof. The medical information can include, for example, information indicative of one or more medical conditions associated with the user, medication usage by the user, or both. The medical information data can further include an Epworth Sleepiness Score (ESS), a multiple sleep latency test (MSLT) test result or score and/or a Pittsburgh Sleep Quality Index (PSQI) score or value. The medical information data can include results from one or more of a polysomnography (PSG) test, a CPAP titration, or a home sleep test (HST), respiratory therapy system settings from one or more sleep sessions, sleep related respiratory events from one or more sleep sessions, or any combination thereof. The self-reported user feedback can include information indicative of a self-reported subjective sleep score (e.g., poor, average, excellent), a self-reported subjective stress level of the user, a self-reported subjective fatigue level of the user, a self-reported subjective health status of the user, a recent life event experienced by the user, or any combination thereof.

The electronic interface 119 is configured to receive data (e.g., physiological data and/or audio data) from the one or more sensors 130 such that the data can be stored in the memory device 114 and/or analyzed by the processor 112 of the control system 110. The received data, such as physiological data, flow rate data, pressure data, motion data, acoustic data, etc., may be used to determine and/or calculate physiological parameters. The electronic interface 119 can communicate with the one or more sensors 130 using a wired connection or a wireless connection (e.g., using an RF communication protocol, a Wi-Fi communication protocol, a Bluetooth communication protocol, an IR communication protocol, over a cellular network, over any other optical communication protocol, etc.). The electronic interface 119 can include an antenna, a receiver (e.g., an RF receiver), a transmitter (e.g., an RF transmitter), a transceiver, or any combination thereof. The electronic interface 119 can also include one more processors and/or one more memory devices that are the same as, or similar to, the processor 112 and the memory device 114 described herein. In some implementations, the electronic interface 119 is coupled to or integrated in the user device 170. In other implementations, the electronic interface 119 is coupled to or integrated (e.g., in a housing) with the control system 110 and/or the memory device 114.

As noted above, in some implementations, the system 100 optionally includes a respiratory therapy system 120. The respiratory therapy system 120 can include a respiratory pressure therapy (RPT) device 122 (referred to herein as respiratory device or respiratory therapy device 122), a user interface 124, a conduit 126 (also referred to as a tube or an air circuit), a display device 128, a humidification tank 129, or any combination thereof. In some implementations, the control system 110, the memory device 114, the display device 128, one or more of the sensors 130, and the humidification tank 129 are part of the respiratory therapy device 122. Respiratory pressure therapy refers to the application of a supply of air to an entrance to a user's airways at a controlled target pressure that is nominally positive with respect to atmosphere throughout the user's breathing cycle (e.g., in contrast to negative pressure therapies such as the tank ventilator or cuirass). The respiratory therapy system 120 is generally used to treat individuals suffering from one or more sleep-related respiratory disorders (e.g., obstructive sleep apnea, central sleep apnea, or mixed sleep apnea).

The respiratory therapy device 122 is generally used to generate pressurized air that is delivered to a user (e.g., using one or more motors that drive one or more compressors). In some implementations, the respiratory therapy device 122 generates continuous constant air pressure that is delivered to the user. In other implementations, the respiratory therapy device 122 generates two or more predetermined pressures (e.g., a first predetermined air pressure and a second predetermined air pressure). In still other implementations, the respiratory therapy device 122 is configured to generate a variety of different air pressures within a predetermined range. For example, the respiratory therapy device 122 can deliver pressurized air at a pressure of at least about 6 cm $H_2O$, at least about 10 cm $H_2O$, at least about 20 cm $H_2O$, between about 6 cm $H_2O$ and about 10 cm $H_2O$, between about 7 cm $H_2O$ and about 12 cm $H_2O$, etc. The respiratory therapy device 122 can also deliver pressurized air at a predetermined flow rate between, for example, about −20 L/min and about 150 L/min, while maintaining a positive pressure (relative to the ambient pressure).

The user interface 124 engages a portion of the user's face and delivers pressurized air from the respiratory therapy device 122 to the user's airway to aid in preventing the airway from narrowing and/or collapsing during sleep. This may also increase the user's oxygen intake during sleep. Generally, the user interface 124 engages the user's face such that the pressurized air is delivered to the user's airway via the user's mouth, the user's nose, or both the user's mouth and nose. Together, the respiratory therapy device 122, the user interface 124, and the conduit 126 form an air pathway fluidly coupled with an airway of the user. The pressurized air also increases the user's oxygen intake during sleep.

Depending upon the therapy to be applied, the user interface 124 may form a seal, for example, with a region or portion of the user's face, to facilitate the delivery of gas at a pressure at sufficient variance with ambient pressure to effect therapy, for example, at a positive pressure of about 10 cm $H_2O$ relative to ambient pressure. For other forms of therapy, such as the delivery of oxygen, the user interface may not include a seal sufficient to facilitate delivery to the airways of a supply of gas at a positive pressure of about 10 cm $H_2O$.

Figure 2:
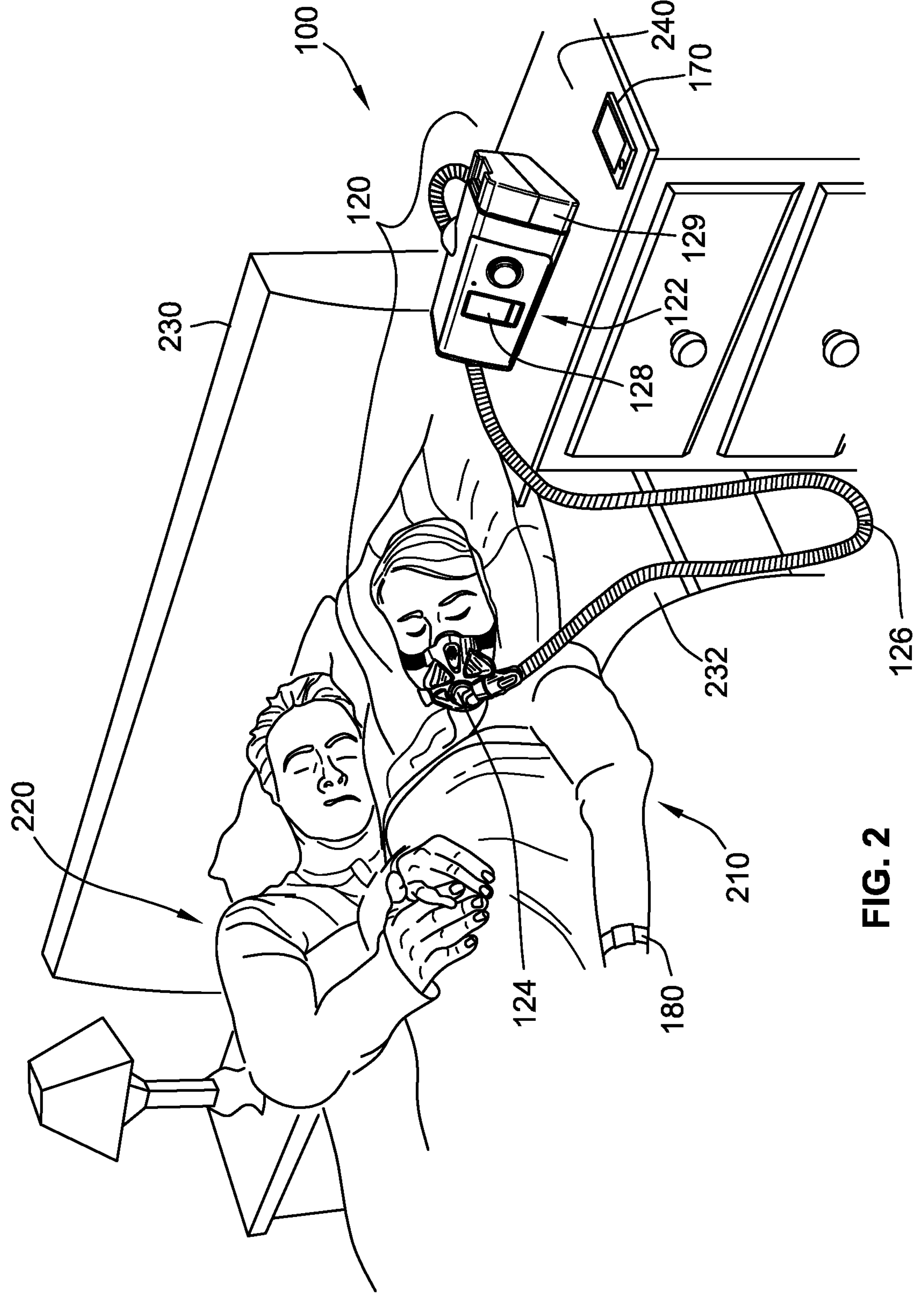
FIG. 2 is a perspective view of at least a portion of the system of FIG. 1, a user, and a bed partner, according to some implementations of the present disclosure.

As shown in FIG. 2, in some implementations, the user interface 124 is a face mask that covers the nose and mouth of the user. Alternatively, in some implementations, the user interface 124 is a nasal mask that provides air to the nose of the user or a nasal pillow mask that delivers air directly to the nostrils of the user. The user interface 124 can include a plurality of straps (e.g., including hook and loop fasteners) for positioning and/or stabilizing the interface on a portion of the user (e.g., the face) and a conformal cushion (e.g., silicone, plastic, foam, etc.) that aids in providing an air-tight seal between the user interface 124 and the user. In some examples, the user interface 124 can be a tube-up mask, wherein straps of the mask are configured to act as conduit (s) to deliver pressurized air to the face or nasal mask. The user interface 124 can also include one or more vents for permitting the escape of carbon dioxide and other gases exhaled by the user 210. In other implementations, the user interface 124 includes a mouthpiece (e.g., a night guard mouthpiece molded to conform to the user's teeth, a mandibular repositioning device, etc.).

The conduit 126 (also referred to as an air circuit or tube) allows the flow of air between two components of the respiratory therapy system 120, such as the respiratory therapy device 122 and the user interface 124. In some implementations, there can be separate limbs of the conduit for inhalation and exhalation. In other implementations, a single limb conduit is used for both inhalation and exhalation.

One or more of the respiratory therapy device 122, the user interface 124, the conduit 126, the display device 128, and the humidification tank 129 can contain one or more sensors (e.g., a pressure sensor, a flow rate sensor, a humidity sensor, a temperature sensor, or more generally any of the other sensors 130 described herein). These one or more sensors can be used, for example, to measure the air pressure and/or flow rate of pressurized air supplied by the respiratory therapy device 122.

The display device 128 is generally used to display image(s) including still images, video images, or both and/or information regarding the respiratory therapy device 122. For example, the display device 128 can provide information regarding the status of the respiratory therapy device 122 (e.g., whether the respiratory therapy device 122 is on/off, the pressure of the air being delivered by the respiratory therapy device 122, the temperature of the air being delivered by the respiratory therapy device 122, etc.) and/or other information (e.g., a sleep score and/or a therapy score (such as a myAir™ score, such as described in WO 2016/061629, which is hereby incorporated by reference herein in its entirety), the current date/time, personal information for the user 210, etc.). In some implementations, the display device 128 acts as a human-machine interface (HMI) that includes a graphic user interface (GUI) configured to display the image(s) as an input interface. The display device 128 can be an LED display, an OLED display, an LCD display, or the like. The input interface can be, for example, a touchscreen or touch-sensitive substrate, a mouse, a keyboard, or any sensor system configured to sense inputs made by a human user interacting with the respiratory therapy device 122.

The humidification tank 129 is coupled to or integrated in the respiratory therapy device 122. The humidification tank 129 includes a reservoir of water that can be used to humidify the pressurized air delivered from the respiratory therapy device 122. The respiratory therapy device 122 can include a heater to heat the water in the humidification tank 129 in order to humidify the pressurized air provided to the user. Additionally, in some implementations, the conduit 126 can also include a heating element (e.g., coupled to and/or imbedded in the conduit 126) that heats the pressurized air delivered to the user. The humidification tank 129 can be fluidly coupled to a water vapor inlet of the air pathway and deliver water vapor into the air pathway via the water vapor inlet, or can be formed in-line with the air pathway as part of the air pathway itself. In other implementations, the respiratory therapy device 122 or the conduit 126 can include a waterless humidifier. The waterless humidifier can incorporate sensors that interface with other sensor positioned elsewhere in system 100.

The respiratory therapy system 120 can be used, for example, as a ventilator or a positive airway pressure (PAP) system such as a continuous positive airway pressure (CPAP) system, an automatic positive airway pressure system (APAP), a bi-level or variable positive airway pressure system (BPAP or VPAP), high-flow therapy (HFT) system, or any combination thereof. The CPAP system delivers a predetermined air pressure (e.g., determined by a sleep physician) to the user. The APAP system automatically varies the air pressure delivered to the user based on, for example, respiration data associated with the user. The BPAP or VPAP system is configured to deliver a first predetermined pressure (e.g., an inspiratory positive airway pressure or IPAP) and a second predetermined pressure (e.g., an expiratory positive airway pressure or EPAP) that is lower than the first predetermined pressure. The HFT system typically provides a continuous, heated, humidified flow of air to an entrance to the airway through an unsealed or open patient interface at a "treatment flow rate" that is held approximately constant throughout the respiratory cycle. The treatment flow rate is nominally set to exceed the patient's peak inspiratory flow rate.

Referring to FIG. 2, a portion of the system 100 (FIG. 1), according to some implementations, is illustrated. A user 210 of the respiratory therapy system 120 and a bed partner 220 are located in a bed 230 and are laying on a mattress 232. The user interface 124 is a facial mask (e.g., a full face mask) that covers the nose and mouth of the user 210. Alternatively, the user interface 124 can be a nasal mask that provides air to the nose of the user 210 or a nasal pillow mask that delivers air directly to the nostrils of the user 210. The user interface 124 can include a plurality of straps (e.g., including hook and loop fasteners) for positioning and/or stabilizing the interface on a portion of the user 210 (e.g., the face) and a conformal cushion (e.g., silicone, plastic, foam, etc.) that aids in providing an air-tight seal between the user interface 124 and the user 210. The user interface 124 can also include one or more vents for permitting the escape of carbon dioxide and other gases exhaled by the user 210. In other implementations, the user interface 124 is a mouthpiece (e.g., a night guard mouthpiece molded to conform to the user's teeth, a mandibular repositioning device, etc.) for directing pressurized air into the mouth of the user 210.

The user interface 124 is fluidly coupled and/or connected to the respiratory therapy device 122 via the conduit 126. In turn, the respiratory therapy device 122 delivers pressurized air to the user 210 via the conduit 126 and the user interface 124 to increase the air pressure in the throat of the user 210 to aid in preventing the airway from closing and/or narrowing during sleep. The respiratory therapy device 122 can be positioned on a nightstand 240 that is directly adjacent to the bed 230 as shown in FIG. 2, or more generally, on any surface or structure that is generally adjacent to the bed 230 and/or the user 210.

Generally, a user who is prescribed usage of the respiratory therapy system 120 will tend to experience higher quality sleep and less fatigue during the day after using the respiratory therapy system 120 during the sleep compared to not using the respiratory therapy system 120 (especially when the user suffers from sleep apnea or other sleep related disorders). For example, the user 210 may suffer from obstructive sleep apnea and rely on the user interface 124 (e.g., a full face mask) to deliver pressurized air from the respiratory therapy device 122 via conduit 126. The respiratory therapy device 122 can be a continuous positive airway pressure (CPAP) machine used to increase air pressure in the throat of the user 210 to prevent the airway from closing and/or narrowing during sleep. For someone with sleep apnea, their airway can narrow or collapse during sleep, reducing oxygen intake, and forcing them to wake up and/or otherwise disrupt their sleep. The CPAP machine prevents the airway from narrowing or collapsing, thus minimizing the occurrences where she wakes up or is otherwise disturbed due to reduction in oxygen intake. While the respiratory therapy device 122 strives to maintain a medically prescribed air pressure or pressures during sleep, the user can experience sleep discomfort due to the therapy.

Referring to back to FIG. 1, the one or more sensors 130 of the system 100 include a pressure sensor 132, a flow rate sensor 134, temperature sensor 136, a motion sensor 138, a microphone 140, a speaker 142, a radio-frequency (RF) receiver 146, a RF transmitter 148, a camera 150, an infrared sensor 152, a photoplethysmogram (PPG) sensor 154, an electrocardiogram (ECG) sensor 156, an electroencephalography (EEG) sensor 158, a capacitive sensor 160, a force sensor 162, a strain gauge sensor 164, an electromyography (EMG) sensor 166, an oxygen sensor 168, an analyte sensor 174, a moisture sensor 176, a Light Detection and Ranging (LiDAR) sensor 178, an electrodermal sensor, an accelerometer, an electrooculography (EOG) sensor, a light sensor, a humidity sensor, an air quality sensor, or any combination thereof. Generally, each of the one or more sensors 130 are configured to output sensor data that is received and stored in the memory device 114 or one or more other memory devices.

While the one or more sensors 130 are shown and described as including each of the pressure sensor 132, the flow rate sensor 134, the temperature sensor 136, the motion sensor 138, the microphone 140, the speaker 142, the RF receiver 146, the RF transmitter 148, the camera 150, the infrared sensor 152, the photoplethysmogram (PPG) sensor 154, the electrocardiogram (ECG) sensor 156, the electroencephalography (EEG) sensor 158, the capacitive sensor 160, the force sensor 162, the strain gauge sensor 164, the electromyography (EMG) sensor 166, the oxygen sensor 168, the analyte sensor 174, the moisture sensor 176, and the LiDAR sensor 178, more generally, the one or more sensors 130 can include any combination and any number of each of the sensors described and/or shown herein.

As described herein, the system 100 generally can be used to generate data (e.g., physiological data, flow rate data, pressure data, motion data, acoustic data, etc.) associated with a user (e.g., a user of the respiratory therapy system 120 shown in FIG. 2) before, during, and/or after a sleep session. The generated data can be analyzed to generate one or more physiological parameters (e.g., before, during, and/or after a sleep session) and/or sleep-related parameters (e.g., during a sleep session), which can include any parameter, measurement, etc. related to the user. Examples of the one or more physiological parameters include a respiration pattern, a respiration rate, an inspiration amplitude, an expiration amplitude, a heart rate, heart rate variability, a length of time between breaths, a time of maximal inspiration, a time of maximal expiration, a forced breath parameter (e.g., distinguishing releasing breath from forced exhalation), respiration variability, breath morphology (e.g., the shape of one or more breaths), movement of the user 210, temperature, EEG activity, EMG activity, ECG data, a sympathetic response parameter, a parasympathetic response parameter, and the like. The one or more sleep-related parameters that can be determined for the user 210 during the sleep session include, for example, an Apnea-Hypopnea Index (AHI) score, a sleep score, a therapy score, a flow signal, a pressure signal, a respiration signal, a respiration pattern, a respiration rate, an inspiration amplitude, an expiration amplitude, an inspiration-expiration ratio, a number of events (e.g., apnea events) per hour, a pattern of events, a sleep state and/or sleep stage, a heart rate, a heart rate variability, movement of the user 210, temperature, EEG activity, EMG activity, arousal, snoring, choking, coughing, whistling, wheezing, or any combination thereof.

The one or more sensors 130 can be used to generate, for example, physiological data, audio data, or both. Physiological data generated by one or more of the sensors 130 can be used by the control system 110 to determine the duration of sleep and sleep quality of user 210. For example, a sleep-wake signal associated with the user 210 during the sleep session and one or more sleep-related parameters. The sleep-wake signal can be indicative of one or more sleep states, including sleep, wakefulness, relaxed wakefulness, micro-awakenings, or distinct sleep stages such as a rapid eye movement (REM) stage, a first non-REM stage (often referred to as "N1"), a second non-REM stage (often referred to as "N2"), a third non-REM stage (often referred to as "N3"), or any combination thereof. Methods for determining sleep states and/or sleep stages from physiological data generated by one or more of the sensors, such as sensors 130, are described in, for example, WO 2014/047310, US 2014/0088373, WO 2017/132726, WO 2019/122413, and WO 2019/122414, each of which is hereby incorporated by reference herein in its entirety.

The sleep-wake signal can also be timestamped to determine a time that the user enters the bed, a time that the user exits the bed, a time that the user attempts to fall asleep, etc. The sleep-wake signal can be measured by the one or more sensors 130 during the sleep session at a predetermined sampling rate, such as, for example, one sample per second, one sample per seconds, one sample per minute, etc. In some implementations, the sleep-wake signal can also be indicative of a respiration signal, a respiration rate, an inspiration amplitude, an expiration amplitude, an inspiration-expiration ratio, a number of events per hour, a pattern of events, pressure settings of the respiratory therapy device 122, or any combination thereof during the sleep session.

The event(s) can include snoring, apneas, central apneas, obstructive apneas, mixed apneas, hypopneas, a mouth leak, a mask leak (e.g., from the user interface 124), a restless leg, a sleeping disorder, choking, an increased heart rate, a heart rate variation, labored breathing, an asthma attack, an epileptic episode, a seizure, a fever, a cough, a sneeze, a snore, a gasp, the presence of an illness such as the common cold or the flu, or any combination thereof. In some implementations, mouth leak can include continuous mouth leak, or valve-like mouth leak (i.e. varying over the breath duration) where the lips of a user, typically using a nasal/nasal pillows mask, pop open on expiration. Mouth leak can lead to dryness of the mouth, bad breath, and is sometimes colloquially referred to as "sandpaper mouth."

The one or more sleep-related parameters that can be determined for the user during the sleep session based on the sleep-wake signal include, for example, sleep quality metrics such as a total time in bed, a total sleep time, a sleep onset latency, a wake-after-sleep-onset parameter, a sleep efficiency, a fragmentation index, or any combination thereof.

The data generated by the one or more sensors 130 (e.g., physiological data, flow rate data, pressure data, motion data, acoustic data, etc.) can also be used to determine a respiration signal. The respiration signal is generally indicative of respiration or breathing of the user. The respiration signal can be indicative of a respiration pattern, which can include, for example, a respiration rate, a respiration rate variability, an inspiration amplitude, an expiration amplitude, an inspiration-expiration ratio, and other respiration-related parameters, as well as any combination thereof. In some cases, during a sleep session, the respiration signal can include a number of events per hour (e.g., during sleep), a pattern of events, pressure settings of the respiratory therapy device 122, or any combination thereof. The event(s) can include snoring, apneas (e.g., central apneas, obstructive apneas, mixed apneas, and hypopneas), a mouth leak, a mask leak (e.g., from the user interface 124), a restless leg, a sleeping disorder, choking, an increased heart rate, labored breathing, an asthma attack, an epileptic episode, a seizure, or any combination thereof.

Generally, the sleep session includes any point in time after the user 210 has laid or sat down in the bed 230 (or another area or object on which they intend to sleep), and/or has turned on the respiratory therapy device 122 and/or donned the user interface 124. The sleep session can thus include time periods (i) when the user 210 is using the CPAP system but before the user 210 attempts to fall asleep (for example when the user 210 lays in the bed 230 reading a book); (ii) when the user 210 begins trying to fall asleep but is still awake; (iii) when the user 210 is in a light sleep (also referred to as stage 1 and stage 2 of non-rapid eye movement (NREM) sleep); (iv) when the user 210 is in a deep sleep (also referred to as slow-wave sleep, SWS, or stage 3 of NREM sleep); (v) when the user 210 is in rapid eye movement (REM) sleep; (vi) when the user 210 is periodically awake between light sleep, deep sleep, or REM sleep; or (vii) when the user 210 wakes up and does not fall back asleep.

The sleep session is generally defined as ending once the user 210 removes the user interface 124, turns off the respiratory therapy device 122, and/or gets out of bed 230. In some implementations, the sleep session can include additional periods of time, or can be limited to only some of the above-disclosed time periods. For example, the sleep session can be defined to encompass a period of time beginning when the respiratory therapy device 122 begins supplying the pressurized air to the airway or the user 210, ending when the respiratory therapy device 122 stops supplying the pressurized air to the airway of the user 210, and including some or all of the time points in between, when the user 210 is asleep or awake.

The pressure sensor 132 outputs pressure data that can be stored in the memory device 114 and/or analyzed by the processor 112 of the control system 110. In some implementations, the pressure sensor 132 is an air pressure sensor (e.g., barometric pressure sensor) that generates sensor data indicative of the respiration (e.g., inhaling and/or exhaling) of the user of the respiratory therapy system 120 and/or ambient pressure. In such implementations, the pressure sensor 132 can be coupled to or integrated in the respiratory therapy device 122, the user interface 124, or the conduit 126. The pressure sensor 132 can be used to determine an air pressure in the respiratory therapy device 122, an air pressure in the conduit 126, an air pressure in the user interface 124, or any combination thereof. The pressure sensor 132 can be, for example, a capacitive sensor, an electromagnetic sensor, an inductive sensor, a resistive sensor, a piezoelectric sensor, a strain-gauge sensor, an optical sensor, a potentiometric sensor, or any combination thereof. In one example, the pressure sensor 132 can be used to determine a blood pressure of a user.

The flow rate sensor 134 outputs flow rate data that can be stored in the memory device 114 and/or analyzed by the processor 112 of the control system 110. In some implementations, the flow rate sensor 134 is used to determine an air flow rate from the respiratory therapy device 122, an air flow rate through the conduit 126, an air flow rate through the user interface 124, or any combination thereof. In such implementations, the flow rate sensor 134 can be coupled to or integrated in the respiratory therapy device 122, the user interface 124, or the conduit 126. The flow rate sensor 134 can be a mass flow rate sensor such as, for example, a rotary flow meter (e.g., Hall effect flow meters), a turbine flow meter, an orifice flow meter, an ultrasonic flow meter, a hot wire sensor, a vortex sensor, a membrane sensor, or any combination thereof.

The flow rate sensor 134 can be used to generate flow rate data associated with the user 210 (FIG. 2) of the respiratory therapy device 122 during the sleep session. Examples of flow rate sensors (such as, for example, the flow rate sensor 134) are described in WO 2012/012835, which is hereby incorporated by reference herein in its entirety. In some implementations, the flow rate sensor 134 is configured to measure a vent flow (e.g., intentional "leak"), an unintentional leak (e.g., mask leak and/or mouth leak, such as detection of mouth leak from flow signals as described in WO 2021/152526, which is hereby incorporated by reference herein in its entirety), a patient flow (e.g., air into and/or out of lungs), or any combination thereof. In some implementations, the flow rate data can be analyzed to determine cardiogenic oscillations of the user.

The temperature sensor 136 outputs temperature data that can be stored in the memory device 114 and/or analyzed by the processor 112 of the control system 110. In some implementations, the temperature sensor 136 generates temperature data indicative of a core body temperature of the user 210 (FIG. 2), a skin temperature of the user 210, a temperature of the air flowing from the respiratory therapy device 122 and/or through the conduit 126, a temperature of the air in the user interface 124, an ambient temperature, or any combination thereof. The temperature sensor 136 can be, for example, a thermocouple sensor, a thermistor sensor, a silicon band gap temperature sensor or semiconductor-based sensor, a resistance temperature detector, or any combination thereof.

The motion sensor 138 outputs motion data that can be stored in the memory device 114 and/or analyzed by the processor 112 of the control system 110. The motion sensor 138 can be used to detect movement of the user 210 during the sleep session, and/or detect movement of any of the components of the respiratory therapy system 120, such as the respiratory therapy device 122, the user interface 124, or the conduit 126. The motion sensor 138 can include one or more inertial sensors, such as accelerometers, gyroscopes, and magnetometers. In some implementations, the motion sensor 138 alternatively or additionally generates one or more signals representing bodily movement of the user, from which may be obtained a signal representing a sleep state or sleep stage of the user; for example, via a respiratory movement of the user. In some implementations, the motion data from the motion sensor 138 can be used in conjunction with additional data from another sensor 130 to determine the sleep state or sleep stage of the user. In some implementations, the motion data can be used to determine a location, a body position, and/or a change in body position of the user.

The microphone 140 outputs audio data that can be stored in the memory device 114 and/or analyzed by the processor 112 of the control system 110. The audio data generated by the microphone 140 is reproducible as one or more sound(s) during a sleep session (e.g., sounds from the user 210). The audio data form the microphone 140 can also be used to identify (e.g., using the control system 110) an event experienced by the user during the sleep session, as described in further detail herein. The microphone 140 can be coupled to or integrated in the respiratory therapy device 122, the user interface 124, the conduit 126, or the user device 170. In some implementations, the system 100 includes a plurality of microphones (e.g., two or more microphones and/or an array of microphones with beamforming) such that sound data generated by each of the plurality of microphones can be used to discriminate the sound data generated by another of the plurality of microphones.

The speaker 142 outputs sound waves. In one or more implementations, the sound waves are audible to a user of the system 100 (e.g., the user 210 of FIG. 2) or inaudible to the user of the system (e.g., ultrasonic sound waves). The speaker 142 can be used, for example, as an alarm clock or to play an alert or message to the user 210 (e.g., in response to an identified body position and/or a change in body position). In some implementations, the speaker 142 can be used to communicate the audio data generated by the microphone 140 to the user. The speaker 142 can be coupled to or integrated in the respiratory therapy device 122, the user interface 124, the conduit 126, or the user device 170.

The microphone 140 and the speaker 142 can be used as separate devices. In some implementations, the microphone 140 and the speaker 142 can be combined into an acoustic sensor 141 (e.g., a SONAR sensor), as described in, for example, WO 2018/050913 and WO 2020/104465, each of which is hereby incorporated by reference herein in its entirety. In such implementations, the speaker 142 generates or emits sound waves at a predetermined interval and/or frequency and the microphone 140 detects the reflections of the emitted sound waves from the speaker 142. In one or more implementations, the sound waves generated or emitted by the speaker 142 can have a frequency that is not audible to the human ear (e.g., below 20 Hz or above around 18 kHz) so as not to disturb the sleep of the user 210 or the bed partner 220 (FIG. 2). Based at least in part on the data from the microphone 140 and/or the speaker 142, the control system 110 can determine a location of the user 210 (FIG. 2) and/or one or more of the sleep-related parameters (e.g., an identified body position and/or a change in body position) and/or respiration-related parameters described in herein such as, for example, a respiration pattern, a respiration signal (from which, e.g., breath morphology may be determined), a respiration rate, an inspiration amplitude, an expiration amplitude, an inspiration-expiration ratio, a number of events per hour, a pattern of events, a sleep state, a sleep stage, or any combination thereof. In this context, a sonar sensor may be understood to concern an active acoustic sensing, such as by generating/transmitting ultrasound or low frequency ultrasound sensing signals (e.g., in a frequency range of about 17-23 kHz, 18-22 kHz, or 17-18 kHz, for example), through the air. Such a system may be considered in relation to WO2018/050913 and WO 2020/104465 mentioned above.

In some cases, a microphone 140 and/or speaker 142 can be incorporated into a separate device, such as body-worn device, such as one or a set of earphones or headphones. In some cases, such a device can include other of the one or more sensors 130.

In some implementations, the sensors 130 include (i) a first microphone that is the same as, or similar to, the microphone 140, and is integrated in the acoustic sensor 141 and (ii) a second microphone that is the same as, or similar to, the microphone 140, but is separate and distinct from the first microphone that is integrated in the acoustic sensor 141.

The RF transmitter 148 generates and/or emits radio waves having a predetermined frequency and/or a predetermined amplitude (e.g., within a high frequency band, within a low frequency band, long wave signals, short wave signals, etc.). The RF receiver 146 detects the reflections of the radio waves emitted from the RF transmitter 148, and this data can be analyzed by the control system 110 to determine a location and/or body position of the user 210 (FIG. 2) and/or one or more of the sleep-related parameters described herein. An RF receiver (either the RF receiver 146 and the RF transmitter 148 or another RF pair) can also be used for wireless communication between the control system 110, the respiratory therapy device 122, the one or more sensors 130, the user device 170, or any combination thereof. While the RF receiver 146 and RF transmitter 148 are shown as being separate and distinct elements in FIG. 1, in some implementations, the RF receiver 146 and RF transmitter 148 are combined as a part of an RF sensor 147 (e.g., a RADAR sensor). In some such implementations, the RF sensor 147 includes a control circuit. The specific format of the RF communication could be Wi-Fi, Bluetooth, etc.

In some implementations, the RF sensor 147 is a part of a mesh system. One example of a mesh system is a Wi-Fi mesh system, which can include mesh nodes, mesh router (s), and mesh gateway(s), each of which can be mobile/movable or fixed. In such implementations, the Wi-Fi mesh system includes a Wi-Fi router and/or a Wi-Fi controller and one or more satellites (e.g., access points), each of which include an RF sensor that the is the same as, or similar to, the RF sensor 147. The Wi-Fi router and satellites continuously communicate with one another using Wi-Fi signals. The Wi-Fi mesh system can be used to generate motion data based on changes in the Wi-Fi signals (e.g., differences in received signal strength) between the router and the satellite (s) due to an object or person moving partially obstructing the signals. The motion data can be indicative of motion, breathing, heart rate, gait, falls, behavior, etc., or any combination thereof.

The camera 150 outputs image data reproducible as one or more images (e.g., still images, video images, thermal images, or a combination thereof) that can be stored in the memory device 114. The image data from the camera 150 can be used by the control system 110 to determine one or more of the sleep-related parameters described herein. The image data from the camera 150 can be used by the control system 110 to determine one or more of the sleep-related parameters described herein, such as, for example, one or more events (e.g., periodic limb movement or restless leg syndrome), a respiration signal, a respiration rate, an inspiration amplitude, an expiration amplitude, an inspiration-expiration ratio, a number of events per hour, a pattern of events, a sleep state, a sleep stage, or any combination thereof. Further, the image data from the camera 150 can be used to identify a location and/or body position of the user, to determine chest movement of the user 210, to determine air flow of the mouth and/or nose of the user 210, to determine a time when the user 210 enters the bed 230 (FIG. 2), and to determine a time when the user 210 exits the bed 230. The camera 150 can also be used to track eye movements, pupil dilation (if one or both of the user 210's eyes are open), blink rate, or any changes during REM sleep.

The infrared (IR) sensor 152 outputs infrared image data reproducible as one or more infrared images (e.g., still images, video images, or both) that can be stored in the memory device 114. The infrared data from the IR sensor 152 can be used to determine one or more sleep-related parameters during a sleep session, including a temperature of the user 210 and/or movement of the user 210. The IR sensor 152 can also be used in conjunction with the camera 150 when measuring the presence, location, and/or movement of the user 210. The IR sensor 152 can detect infrared light having a wavelength between about 700 nm and about 1 mm, for example, while the camera 150 can detect visible light having a wavelength between about 380 nm and about 740 nm.

The PPG sensor 154 outputs physiological data associated with the user 210 (FIG. 2) that can be used to determine one or more sleep-related parameters, such as, for example, a heart rate, a heart rate pattern, a heart rate variability, a cardiac cycle, respiration rate, an inspiration amplitude, an expiration amplitude, an inspiration-expiration ratio, estimated blood pressure parameter(s), or any combination thereof. The PPG sensor 154 can be worn by the user 210, embedded in clothing and/or fabric that is worn by the user 210, embedded in and/or coupled to the user interface 124 and/or its associated headgear (e.g., straps, etc.), etc. In some cases, the PPG sensor 154 can be a non-contact PPG sensor capable of PPG at a distance. In some cases, a PPG sensor 154 can be used in the determination of a pulse arrival time (PAT). PAT can be a determination of the time interval needed for a pulse wave to travel from the heart to a distal location on the body, such as a finger or other location. In other words, the PAT can be determined by measuring the time interval between the R wave of an ECG and a peak of the PPG. In some cases, baseline changes in the PPG signal can be used to derive a respiratory signal, and thus respiratory information, such as respiratory rate. In some cases, the PPG signal can provide SpO2 data, which can be used in the detection of sleep-related disorders, such as OSA.

The ECG sensor 156 outputs physiological data associated with electrical activity of the heart of the user 210. In some implementations, the ECG sensor 156 includes one or more electrodes that are positioned on or around a portion of the user 210 during the sleep session. The physiological data from the ECG sensor 156 can be used, for example, to determine one or more of the sleep-related parameters described herein. In some cases, the amplitude and/or morphology changes in the ECG electrical trace can be used to identify a breathing curve, and thus respiratory information, such as a respiratory rate.

In some cases, an ECG signal and/or a PPG signal can be used in concert with a secondary estimate of parasympathetic and/or sympathetic innervation, such as via a galvanic skin response (GSR) sensor. Such signals can be used to identify what actual breathing curve is occurring, and if it has a positive, neutral, or negative impact on the stress level of the individual.

The EEG sensor 158 outputs physiological data associated with electrical activity of the brain of the user 210. In some implementations, the EEG sensor 158 includes one or more electrodes that are positioned on or around the scalp of the user 210 during the sleep session. The physiological data from the EEG sensor 158 can be used, for example, to determine a sleep state or sleep stage of the user 210 at any given time during the sleep session. In some implementations, the EEG sensor 158 can be integrated in the user interface 124 and/or the associated headgear (e.g., straps, etc.).

The capacitive sensor 160, the force sensor 162, and the strain gauge sensor 164 output data that can be stored in the memory device 114 and used by the control system 110 to determine one or more of the sleep-related parameters described herein. The EMG sensor 166 outputs physiological data associated with electrical activity produced by one or more muscles. The oxygen sensor 168 outputs oxygen data indicative of an oxygen concentration of gas (e.g., in the conduit 126 or at the user interface 124). The oxygen sensor 168 can be, for example, an ultrasonic oxygen sensor, an electrical oxygen sensor, a chemical oxygen sensor, an optical oxygen sensor, or any combination thereof. In some implementations, the one or more sensors 130 also include a galvanic skin response (GSR) sensor, a blood flow sensor, a respiration sensor, a pulse sensor, a sphygmomanometer sensor, an oximetry sensor, or any combination thereof.

The analyte sensor 174 can be used to detect the presence of an analyte in the exhaled breath of the user 210. The data output by the analyte sensor 174 can be stored in the memory device 114 and used by the control system 110 to determine the identity and concentration of any analytes in the breath of the user 210. In some implementations, the analyte sensor 174 is positioned near a mouth of the user 210 to detect analytes in breath exhaled from the user 210's mouth. For example, when the user interface 124 is a face mask that covers the nose and mouth of the user 210, the analyte sensor 174 can be positioned within the face mask to monitor the user 210's mouth breathing. In other implementations, such as when the user interface 124 is a nasal mask or a nasal pillow mask, the analyte sensor 174 can be positioned near the nose of the user 210 to detect analytes in breath exhaled through the user's nose. In still other implementations, the analyte sensor 174 can be positioned near the user 210's mouth when the user interface 124 is a nasal mask or a nasal pillow mask. In this implementation, the analyte sensor 174 can be used to detect whether any air is inadvertently leaking from the user 210's mouth. In some implementations, the analyte sensor 174 is a volatile organic compound (VOC) sensor that can be used to detect carbon-based chemicals or compounds. In some implementations, the analyte sensor 174 can also be used to detect whether the user 210 is breathing through their nose or mouth. For example, if the data output by an analyte sensor 174 positioned near the mouth of the user 210 or within the face mask (in implementations where the user interface 124 is a face mask) detects the presence of an analyte, the control system 110 can use this data as an indication that the user 210 is breathing through their mouth.

The moisture sensor 176 outputs data that can be stored in the memory device 114 and used by the control system 110. The moisture sensor 176 can be used to detect moisture in various areas surrounding the user (e.g., inside the conduit 126 or the user interface 124, near the user 210's face, near the connection between the conduit 126 and the user interface 124, near the connection between the conduit 126 and the respiratory therapy device 122, etc.). Thus, in some implementations, the moisture sensor 176 can be positioned in the user interface 124 or in the conduit 126 to monitor the humidity of the pressurized air from the respiratory therapy device 122. In other implementations, the moisture sensor 176 is placed near any area where moisture levels need to be monitored. The moisture sensor 176 can also be used to monitor the humidity of the ambient environment surrounding the user 210, for example, the air inside the bedroom of the user 210. The moisture sensor 176 can also be used to track the user 210's biometric response to environmental changes.

One or more Light Detection and Ranging (LiDAR) sensors 178 can be used for depth sensing. This type of optical sensor (e.g., laser sensor) can be used to detect objects and build three dimensional (3D) maps of the surroundings, such as of a living space. LiDAR can generally utilize a pulsed laser to make time of flight measurements. LiDAR is also referred to as 3D laser scanning. In an example of use of such a sensor, a fixed or mobile device (such as a smartphone) having a LiDAR sensor 178 can measure and map an area extending 5 meters or more away from the sensor. The LiDAR data can be fused with point cloud data estimated by an electromagnetic RADAR sensor, for example. The LiDAR sensor(s) 178 may also use artificial intelligence (AI) to automatically geofence RADAR systems by detecting and classifying features in a space that might cause issues for RADAR systems, such a glass windows (which can be highly reflective to RADAR). LiDAR can also be used to provide an estimate of the height of a person, as well as changes in height when the person sits down, or falls down, for example. LiDAR may be used to form a 3D mesh representation of an environment. In a further use, for solid surfaces through which radio waves pass (e.g., radio-translucent materials), the LiDAR may reflect off such surfaces, thus allowing a classification of different type of obstacles.

In some implementations, the one or more sensors 130 also include a galvanic skin response (GSR) sensor, a blood flow sensor, a respiration sensor, a pulse sensor, a sphygmomanometer sensor, an oximetry sensor, a sonar sensor, a RADAR sensor, a blood glucose sensor, a color sensor, a pH sensor, an air quality sensor, a tilt sensor, an orientation sensor, a rain sensor, a soil moisture sensor, a water flow sensor, an alcohol sensor, or any combination thereof.

While shown separately in FIG. 1, any combination of the one or more sensors 130 can be integrated in and/or coupled to any one or more of the components of the system 100, including the respiratory therapy device 122, the user interface 124, the conduit 126, the humidification tank 129, the control system 110, the user device 170, or any combination thereof. For example, the microphone 140 and speaker 142 is integrated in and/or coupled to the user device 170 and the pressure sensor 130 and/or flow rate sensor 132 are integrated in and/or coupled to the respiratory therapy device 122. In some implementations, at least one of the one or more sensors 130 is not coupled to the respiratory therapy device 122, the control system 110, or the user device 170, and is positioned generally adjacent to the user 210 during the sleep session (e.g., positioned on or in contact with a portion of the user 210, worn by the user 210, coupled to or positioned on the nightstand, coupled to the mattress, coupled to the ceiling, etc.).

The data from the one or more sensors 130 can be analyzed to determine one or more physiological parameters, which can include a respiration signal, a respiration rate, a respiration pattern or morphology, respiration rate variability, an inspiration amplitude, an expiration amplitude, an inspiration-expiration ratio, a length of time between breaths, a time of maximal inspiration, a time of maximal expiration, a forced breath parameter (e.g., distinguishing releasing breath from forced exhalation), an occurrence of one or more events, a number of events per hour, a pattern of events, a sleep state, a sleep stage, an apnea-hypopnea index (AHI), a heart rate, heart rate variability, movement of the user 210, temperature, EEG activity, EMG activity, ECG data, a sympathetic response parameter, a parasympathetic response parameter or any combination thereof. The one or more events can include snoring, apneas, central apneas, obstructive apneas, mixed apneas, hypopneas, an intentional mask leak, an unintentional mask leak, a mouth leak, a cough, a restless leg, a sleeping disorder, choking, an increased heart rate, labored breathing, an asthma attack, an epileptic episode, a seizure, increased blood pressure, or any combination thereof. Many of these physiological parameters are sleep-related parameters, although in some cases the data from the one or more sensors 130 can be analyzed to determine one or more non-physiological parameters, such as non-physiological sleep-related parameters. Non-physiological parameters can also include operational parameters of the respiratory therapy system, including flow rate, pressure, humidity of the pressurized air, speed of motor, etc. Other types of physiological and non-physiological parameters can also be determined, either from the data from the one or more sensors 130, or from other types of data.

The user device 170 (FIG. 1) includes a display device 172. The user device 170 can be, for example, a mobile device such as a smart phone, a tablet, a laptop, or the like. Alternatively, the user device 170 can be an external sensing system, a television (e.g., a smart television) or another smart home device (e.g., a smart speaker(s) such as Google Nest Hub, Google Home, Amazon Show, Amazon Echo, Alexa™-enabled devices, etc.). In some implementations, the user device is a wearable device (e.g., a smart watch). The display device 172 is generally used to display image(s) including still images, video images, or both. In some implementations, the display device 172 acts as a human-machine interface (HMI) that includes a graphic user interface (GUI) configured to display the image(s) and an input interface. The display device 172 can be an LED display, an OLED display, an LCD display, or the like. The input interface can be, for example, a touchscreen or touch-sensitive substrate, a mouse, a keyboard, or any sensor system configured to sense inputs made by a human user interacting with the user device 170. In some implementations, one or more user devices can be used by and/or included in the system 100.

The activity tracker 180 is generally used to aid in generating physiological data for determining an activity measurement associated with the user. The activity measurement can include, for example, a number of steps, a distance traveled, a number of steps climbed, a duration of physical activity, a type of physical activity, an intensity of physical activity, time spent standing, a respiration rate, an average respiration rate, a resting respiration rate, a maximum respiration rate, a respiration rate variability, a heart rate, an average heart rate, a resting heart rate, a maximum heart rate, a heart rate variability, a number of calories burned, blood oxygen saturation level (SpO2), electrodermal activity (also known as skin conductance or galvanic skin response), a position of the user, a posture of the user, or any combination thereof. The activity tracker 180 includes one or more of the sensors 130 described herein, such as, for example, the motion sensor 138 (e.g., one or more accelerometers and/or gyroscopes), the PPG sensor 154, and/or the ECG sensor 156.

In some implementations, the activity tracker 180 is a wearable device that can be worn by the user, such as a smartwatch, a wristband, a ring, or a patch. For example, referring to FIG. 2, the activity tracker 180 is worn on a wrist of the user 210. The activity tracker 180 can also be coupled to or integrated a garment or clothing that is worn by the user. Alternatively still, the activity tracker 180 can also be coupled to or integrated in (e.g., within the same housing) the user device 170. More generally, the activity tracker 180 can be communicatively coupled with, or physically integrated in (e.g., within a housing), the control system 110, the memory 114, the respiratory therapy system 120, and/or the user device 170.

The system 100 further includes one or more external devices 190 that affect the environment of the user. The devices 190 can include, in some implementations, the respiratory therapy system 120. The devices 190 can include, in some implementations, the activity tracker 180. The devices 190 can include, in some implementations, the user device 170. The devices 190 can include a thermostat, an air conditioning system, a fan, a heater, a lighting system, a speaker, motorized blinds, motorized curtains, a humidification system, a massage system, a bed vibration system, an adjustable bed frame, an adjustable pillow, an adjustable mattress, a bed temperature regulation system, an adjustable sheet or blanket system, or any combination thereof. The devices 190 can include a door(s) of a room, a window(s) of a room, window blinds or curtains, etc. The devices 190 can allow automatic adjustment of the environment of the user (e.g., automatically setting a thermostat to a specific temperature to adjust ambient temperature around the user). The devices 190 can be manually adjusted (e.g., the user can be prompted on the user device 170 to close window blinds). The lighting system can include smart blinds.

While the control system 110 and the memory device 114 are described and shown in FIG. 1 as being a separate and distinct component of the system 100, in some implementations, the control system 110 and/or the memory device 114 are integrated in the user device 170, the activity tracker 180, the external devices 190, and/or the respiratory therapy device 122. Alternatively, in some implementations, the control system 110 or a portion thereof (e.g., the processor 112) can be located in a cloud (e.g., integrated in a server, integrated in an Internet of Things (IoT) device, connected to the cloud, be subject to edge cloud processing, etc.), located in one or more servers (e.g., remote servers, local servers, etc.), or any combination thereof.

While system 100 is shown as including all of the components described above, more or fewer components can be included in a system for modifying the environment of the user according to implementations of the present disclosure. For example, a first alternative system includes the control system 110, the memory device 114, the devices 190, and at least one of the one or more sensors 130. As another example, a second alternative system includes the control system 110, the memory device 114, at least one of the one or more sensors 130, the devices 190, and the user device 170. As yet another example, a third alternative system includes the control system 110, the memory device 114, the respiratory therapy system 120, at least one of the one or more sensors 130, the activity tracker 180, the devices 190, and the user device 170. Thus, various systems can be formed using any portion or portions of the components shown and described herein and/or in combination with one or more other components.

Figure 3:
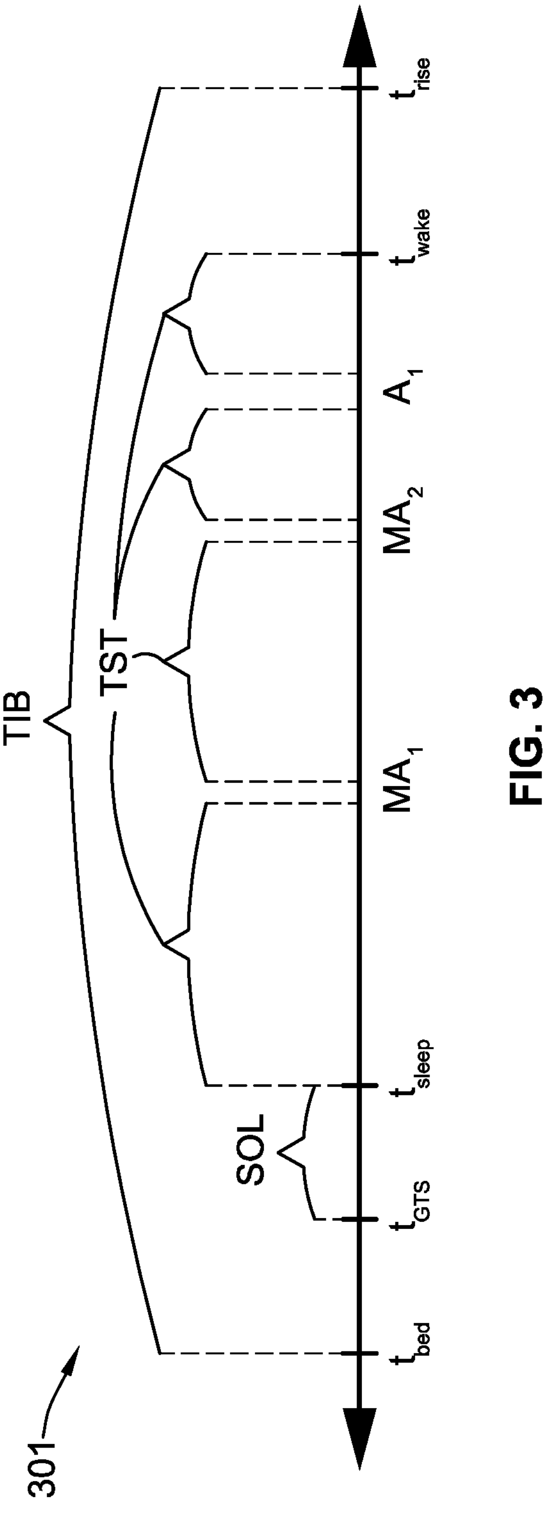
FIG. 3 illustrates an exemplary timeline for a sleep session, according to some implementations of the present disclosure.

As used herein, a sleep session can be defined in a number of ways based on, for example, an initial start time and an end time. Referring to FIG. 3, an exemplary timeline 301 for a sleep session is illustrated. The timeline 300 includes an enter bed time (teed), a go-to-sleep time ($t_{GTS}$), an initial sleep time ($t_{sleep}$), a first micro-awakening $MA_1$ and a second micro-awakening $MA_2$, a wake-up time ($t_{wake}$), and a rising time ($t_{rise}$).

As used herein, a sleep session can be defined in multiple ways. For example, a sleep session can be defined by an initial start time and an end time. In some implementations, a sleep session is a duration where the user is asleep. In such implementations, the sleep session has a start time and an end time, and during the sleep session, the user does not wake until the end time. That is, any period of the user being awake is not included in a sleep session. From this first definition of sleep session, if the user wakes ups and falls asleep multiple times in the same night, each of the sleep intervals separated by an awake interval is a sleep session.

Alternatively, in some implementations, a sleep session has a start time and an end time, and during the sleep session, the user can wake up, without the sleep session ending, so long as a continuous duration that the user is awake is below an awake duration threshold. The awake duration threshold can be defined as a percentage of a sleep session. The awake duration threshold can be, for example, about twenty percent of the sleep session, about fifteen percent of the sleep session duration, about ten percent of the sleep session duration, about five percent of the sleep session duration, about two percent of the sleep session duration, etc., or any other threshold percentage. In some implementations, the awake duration threshold is defined as a fixed amount of time, such as, for example, about one hour, about thirty minutes, about fifteen minutes, about ten minutes, about five minutes, about two minutes, etc., or any other amount of time.

In some implementations, a sleep session is defined as the entire time between the time in the evening at which the user first entered the bed, and the time the next morning when user last left the bed. Put another way, a sleep session can be defined as a period of time that begins on a first date (e.g., Monday, Jan. 6, 2020) at a first time (e.g., 10:00 PM), that can be referred to as the current evening, when the user first enters a bed with the intention of going to sleep (e.g., not if the user intends to first watch television or play with a smart phone before going to sleep, etc.), and ends on a second date (e.g., Tuesday, Jan. 7, 2020) at a second time (e.g., 7:00 AM), that can be referred to as the next morning, when the user first exits the bed with the intention of not going back to sleep that next morning.

In some implementations, the user can manually define the beginning of a sleep session and/or manually terminate a sleep session. For example, the user can select (e.g., by clicking or tapping) one or more user-selectable element that is displayed on the display device 172 of the user device 170 (FIG. 1) to manually initiate or terminate the sleep session.

The enter bed time $t_{bed}$ is associated with the time that the user initially enters the bed (e.g., bed 230 in FIG. 2) prior to falling asleep (e.g., when the user lies down or sits in the bed). The enter bed time $t_{bed}$ can be identified based on a bed threshold duration to distinguish between times when the user enters the bed for sleep and when the user enters the bed for other reasons (e.g., to watch TV). For example, the bed threshold duration can be at least about 10 minutes, at least about 20 minutes, at least about 30 minutes, at least about 45 minutes, at least about 1 hour, at least about 2 hours, etc. While the enter bed time $t_{bed}$ is described herein in reference to a bed, more generally, the enter time $t_{bed}$ can refer to the time the user initially enters any location for sleeping (e.g., a couch, a chair, a sleeping bag, etc.).

The go-to-sleep time (GTS) is associated with the time that the user initially attempts to fall asleep after entering the bed ($t_{bed}$). For example, after entering the bed, the user may engage in one or more activities to wind down prior to trying to sleep (e.g., reading, watching TV, listening to music, using the user device 170, etc.). The initial sleep time ($t_{sleep}$) is the time that the user initially falls asleep. For example, the initial sleep time ($t_{sleep}$) can be the time that the user initially enters the first non-REM sleep stage.

The wake-up time $t_{wake}$ is the time associated with the time when the user wakes up without going back to sleep (e.g., as opposed to the user waking up in the middle of the night and going back to sleep). The user may experience one of more unconscious microawakenings (e.g., microawakenings $MA_1$ and $MA_2$) having a short duration (e.g., 4 seconds, 10 seconds, seconds, 1 minute, etc.) after initially falling asleep. In contrast to the wake-up time $t_{wake}$, the user goes back to sleep after each of the microawakenings $MA_1$ and $MA_2$. Similarly, the user may have one or more conscious awakenings (e.g., awakening A) after initially falling asleep (e.g., getting up to go to the bathroom, attending to children or pets, sleep walking, etc.). However, the user goes back to sleep after the awakening A. Thus, the wake-up time $t_{wake}$ can be defined, for example, based on a wake threshold duration (e.g., the user is awake for at least minutes, at least 20 minutes, at least 30 minutes, at least 1 hour, etc.).

Similarly, the rising time $t_{rise}$ is associated with the time when the user exits the bed and stays out of the bed with the intent to end the sleep session (e.g., as opposed to the user getting up during the night to go to the bathroom, to attend to children or pets, sleep walking, etc.). In other words, the rising time $t_{rise}$ is the time when the user last leaves the bed without returning to the bed until a next sleep session (e.g., the following evening). Thus, the rising time $t_{rise}$ can be defined, for example, based on a rise threshold duration (e.g., the user has left the bed for at least 15 minutes, at least 20 minutes, at least 30 minutes, at least 1 hour, etc.). The enter bed time $t_{bed}$ time for a second, subsequent sleep session can also be defined based on a rise threshold duration (e.g., the user has left the bed for at least 4 hours, at least 6 hours, at least 8 hours, at least 12 hours, etc.).

As described above, the user may wake up and get out of bed one more times during the night between the initial $t_{bed}$ and the final $t_{rise}$. In some implementations, the final wake-up time $t_{wake}$ and/or the final rising time $t_{rise}$ that are identified or determined based on a predetermined threshold duration of time subsequent to an event (e.g., falling asleep or leaving the bed). Such a threshold duration can be customized for the user. For a standard user which goes to bed in the evening, then wakes up and goes out of bed in the morning any period (between the user waking up ($t_{wake}$) or raising up ($t_{rise}$), and the user either going to bed ($t_{bed}$), going to sleep ($t_{GTS}$) or falling asleep ($t_{sleep}$) of between about 12 and about 18 hours can be used. For users that spend longer periods of time in bed, shorter threshold periods may be used (e.g., between about 8 hours and about 14 hours). The threshold period may be initially selected and/or later adjusted based on the system monitoring the user's sleep behavior.

The total time in bed (TIB) is the duration of time between the time enter bed time $t_{bed}$ and the rising time $t_{rise}$. The total sleep time (TST) is associated with the duration between the initial sleep time and the wake-up time, excluding any conscious or unconscious awakenings and/or micro-awakenings therebetween. Generally, the total sleep time (TST) will be shorter than the total time in bed (TIB) (e.g., one minute short, ten minutes shorter, one hour shorter, etc.). For example, referring to the timeline 301 of FIG. 3, the total sleep time (TST) spans between the initial sleep time $t_{sleep}$ and the wake-up time $t_{wake}$, but excludes the duration of the first micro-awakening $MA_1$, the second micro-awakening $MA_2$, and the awakening A. As shown, in this example, the total sleep time (TST) is shorter than the total time in bed (TIB).

In some implementations, the total sleep time (TST) can be defined as a persistent total sleep time (PTST). In such implementations, the persistent total sleep time excludes a predetermined initial portion or period of the first non-REM stage (e.g., light sleep stage). For example, the predetermined initial portion can be between about 30 seconds and about 20 minutes, between about 1 minute and about 10 minutes, between about 3 minutes and about 5 minutes, etc. The persistent total sleep time is a measure of sustained sleep, and smooths the sleep-wake hypnogram. For example, when the user is initially falling asleep, the user may be in the first non-REM stage for a very short time (e.g., about 30 seconds), then back into the wakefulness stage for a short period (e.g., one minute), and then goes back to the first non-REM stage. In this example, the persistent total sleep time excludes the first instance (e.g., about 30 seconds) of the first non-REM stage.

In some implementations, the sleep session is defined as starting at the enter bed time (teed) and ending at the rising time ($t_{rise}$), i.e., the sleep session is defined as the total time in bed (TIB). In some implementations, a sleep session is defined as starting at the initial sleep time ($t_{sleep}$) and ending at the wake-up time ($t_{wake}$). In some implementations, the sleep session is defined as the total sleep time (TST). In some implementations, a sleep session is defined as starting at the go-to-sleep time ($t_{GTS}$) and ending at the wake-up time ($t_{wake}$). In some implementations, a sleep session is defined as starting at the go-to-sleep time ($t_{GTS}$) and ending at the rising time ($t_{rise}$). In some implementations, a sleep session is defined as starting at the enter bed time (bed) and ending at the wake-up time ($t_{wake}$). In some implementations, a sleep session is defined as starting at the initial sleep time ($t_{sleep}$) and ending at the rising time ($t_{rise}$).

Figure 4:
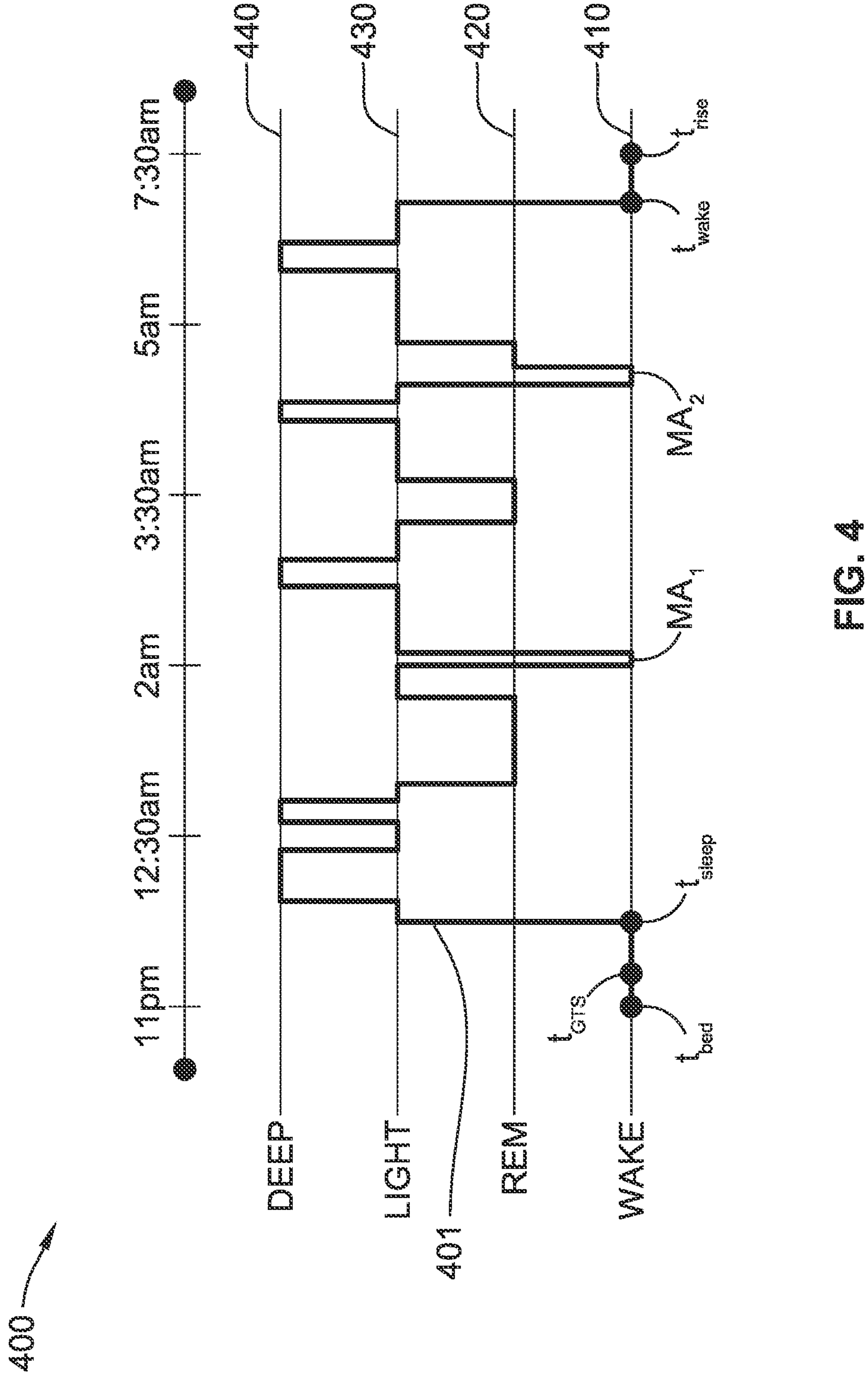
FIG. 4 illustrates an exemplary hypnogram associated with the sleep session of FIG. 3, according to some implementations of the present disclosure.

Referring to FIG. 4, an exemplary hypnogram 400 corresponding to the timeline 300 (FIG. 3), according to some implementations, is illustrated. As shown, the hypnogram 400 includes a sleep-wake signal 401, a wakefulness stage axis 410, a REM stage axis 420, a light sleep stage axis 430, and a deep sleep stage axis 440. The intersection between the sleep-wake signal 401 and one of the axes 410-440 is indicative of the sleep stage at any given time during the sleep session.

The sleep-wake signal 401 can be generated based on physiological data associated with the user (e.g., generated by one or more of the sensors 130 described herein). The sleep-wake signal can be indicative of one or more sleep states, including wakefulness, relaxed wakefulness, micro-awakenings, a REM stage, a first non-REM stage, a second non-REM stage, a third non-REM stage, or any combination thereof. In some implementations, one or more of the first non-REM stage, the second non-REM stage, and the third non-REM stage can be grouped together and categorized as a light sleep stage or a deep sleep stage. For example, the light sleep stage can include the first non-REM stage and the deep sleep stage can include the second non-REM stage and the third non-REM stage. While the hypnogram 400 is shown in FIG. 4 as including the light sleep stage axis 430 and the deep sleep stage axis 440, in some implementations, the hypnogram 400 can include an axis for each of the first non-REM stage, the second non-REM stage, and the third non-REM stage. In other implementations, the sleep-wake signal can also be indicative of a respiration signal, a respiration rate, an inspiration amplitude, an expiration amplitude, an inspiration-expiration ratio, a number of events per hour, a pattern of events, or any combination thereof. Information describing the sleep-wake signal can be stored in the memory device 114.

The hypnogram 400 can be used to determine one or more sleep-related parameters, such as, for example, a sleep onset latency (SOL), wake-after-sleep onset (WASO), a sleep efficiency (SE), a sleep fragmentation index, sleep blocks, or any combination thereof.

The sleep onset latency (SOL) is defined as the time between the go-to-sleep time ($t_{GTS}$) and the initial sleep time ($t_{sleep}$). In other words, the sleep onset latency is indicative of the time that it took the user to actually fall asleep after initially attempting to fall asleep. In some implementations, the sleep onset latency is defined as a persistent sleep onset latency (PSOL). The persistent sleep onset latency differs from the sleep onset latency in that the persistent sleep onset latency is defined as the duration time between the go-to-sleep time and a predetermined amount of sustained sleep. In some implementations, the predetermined amount of sustained sleep can include, for example, at least 10 minutes of sleep within the second non-REM stage, the third non-REM stage, and/or the REM stage with no more than 2 minutes of wakefulness, the first non-REM stage, and/or movement therebetween. In other words, the persistent sleep onset latency requires up to, for example, 8 minutes of sustained sleep within the second non-REM stage, the third non-REM stage, and/or the REM stage. In other implementations, the predetermined amount of sustained sleep can include at least 10 minutes of sleep within the first non-REM stage, the second non-REM stage, the third non-REM stage, and/or the REM stage subsequent to the initial sleep time. In such implementations, the predetermined amount of sustained sleep can exclude any micro-awakenings (e.g., a ten second micro-awakening does not restart the 10-minute period).

The wake-after-sleep onset (WASO) is associated with the total duration of time that the user is awake between the initial sleep time and the wake-up time. Thus, the wake-after-sleep onset includes short and micro-awakenings during the sleep session (e.g., the micro-awakenings $MA_1$ and $MA_2$ shown in FIG. 4), whether conscious or unconscious. In some implementations, the wake-after-sleep onset (WASO) is defined as a persistent wake-after-sleep onset (PWASO) that only includes the total durations of awakenings having a predetermined length (e.g., greater than 10 seconds, greater than 30 seconds, greater than 60 seconds, greater than about 5 minutes, greater than about 10 minutes, etc.)

The sleep efficiency (SE) is determined as a ratio of the total time in bed (TIB) and the total sleep time (TST). For example, if the total time in bed is 8 hours and the total sleep time is 7.5 hours, the sleep efficiency for that sleep session is 93.75%. The sleep efficiency is indicative of the sleep hygiene of the user. For example, if the user enters the bed and spends time engaged in other activities (e.g., watching TV) before sleep, the sleep efficiency will be reduced (e.g., the user is penalized). In some implementations, the sleep efficiency (SE) can be calculated based on the total time in bed (TIB) and the total time that the user is attempting to sleep. In such implementations, the total time that the user is attempting to sleep is defined as the duration between the go-to-sleep (GTS) time and the rising time described herein. For example, if the total sleep time is 8 hours (e.g., between 11 PM and 7 AM), the go-to-sleep time is 10:45 PM, and the rising time is 7:15 AM, in such implementations, the sleep efficiency parameter is calculated as about 94%.

The fragmentation index is determined based at least in part on the number of awakenings during the sleep session. For example, if the user had two micro-awakenings (e.g., micro-awakening $MA_1$ and micro-awakening $MA_2$ shown in FIG. 4), the fragmentation index can be expressed as 2. In some implementations, the fragmentation index is scaled between a predetermined range of integers (e.g., between 0 and 10).

The sleep blocks are associated with a transition between any stage of sleep (e.g., the first non-REM stage, the second non-REM stage, the third non-REM stage, and/or the REM) and the wakefulness stage. The sleep blocks can be calculated at a resolution of, for example, 30 seconds.

In some implementations, the systems and methods described herein can include generating or analyzing a hypnogram including a sleep-wake signal to determine or identify the enter bed time (teed), the go-to-sleep time ($t_{GTS}$), the initial sleep time ($t_{sleep}$), one or more first microawakenings (e.g., $MA_1$ and $MA_2$), the wake-up time ($t_{wake}$), the rising time ($t_{rise}$), or any combination thereof based at least in part on the sleep-wake signal of a hypnogram.

In other implementations, one or more of the sensors 130 can be used to determine or identify the enter bed time (teed), the go-to-sleep time ($t_{GTS}$), the initial sleep time ($t_{sleep}$), one or more first micro-awakenings (e.g., $MA_1$ and $MA_2$), the wake-up time ($t_{wake}$), the rising time ($t_{rise}$), or any combination thereof, which in turn define the sleep session. For example, the enter bed time teed can be determined based on, for example, data generated by the motion sensor 138, the microphone 140, the camera 150, or any combination thereof. The go-to-sleep time can be determined based on, for example, data from the motion sensor 138 (e.g., data indicative of no movement by the user), data from the camera 150 (e.g., data indicative of no movement by the user and/or that the user has turned off the lights), data from the microphone 140 (e.g., data indicative of the using turning off a TV), data from the user device 170 (e.g., data indicative of the user no longer using the user device 170), data from the pressure sensor 132 and/or the flow rate sensor 134 (e.g., data indicative of the user turning on the respiratory therapy device 122, data indicative of the user donning the user interface 124, etc.), or any combination thereof.

Figure 5:
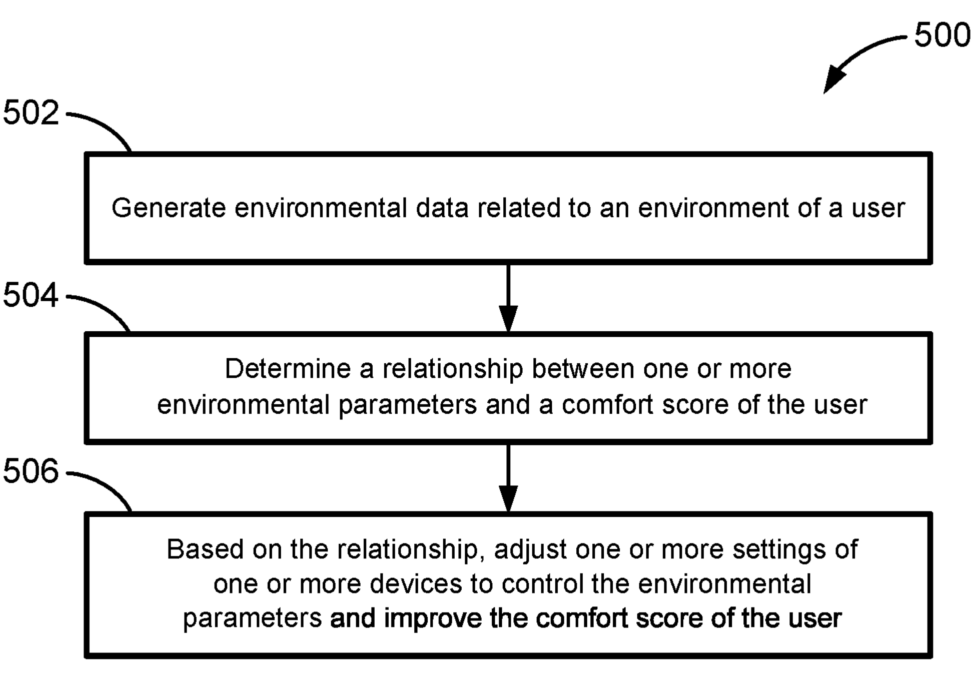
FIG. 5 is a process flow diagram for a method for modifying an environment of a user, according to some implementations of the present disclosure.

Referring to FIG. 5, a method 500 for adjusting settings in an environment of a user according to some implementations of the present disclosure is illustrated. One or more steps or aspects of the method 500 can be implemented using any portion or aspect of the system 100 described herein.

Step 502 of the method 500 includes generating environmental data related to an environment of a user. The environmental data can be generated by any of the one or more sensors 130 of FIG. 1. The environmental data includes values for one or more environmental parameters. For example, the environmental data includes values or data indicating a temperature of the environment of the user, a humidity of the environment of the user, a luminosity of the environment of the user, a noise level in the environment of the user, a noise pattern in the environment of the user, or any combination thereof. The noise pattern can include a frequency of noise, a type of noise (e.g., noise generated by strong winds, intermittent and irregular car horns, regular smoke alarm beep reminders, etc.). The noise level and/or pattern can include noise due to the operation of a respiratory system, such as motor noise, respiration (via a user interface) sounds, mask leak, mouth leak, etc. Such noises can be detected by a microphone, such as a microphone in a smart speaker, smartphone, or a microphone within or otherwise associated with a respiratory therapy device, such as described herein. In some implementations, the temperature of the environment is obtained by a thermostat (e.g., a thermostat of a central air conditioning system), a thermometer, etc. The temperature can be quoted or measured in Fahrenheit, Celsius, Kelvin, etc. In some implementations, the humidity of the environment is obtained by a hygrometer. An air quality sensor can determine particulates or carbon dioxide, carbon monoxide or any other gas in the air. In some implementations, the luminosity of the environment is obtained by a light-dependent resistor, a photoresistor, or any other light sensor. The environment of the user can include a living room, a bedroom, an office space, a dining room, etc.

Step 504 of the method 500 includes analyzing the environmental data from step 502 to determine a relationship between one or more environmental parameters within the environmental data and a comfort score of the user. The one or more environmental parameters can include a temperature of the environment of the user, a humidity of the environment of the user, a luminosity of the environment of the user, a noise level in the environment of the user, a noise pattern in the environment of the user, or any combination thereof.

The comfort score of the user is indicative of a comfort level of the user. In some implementations, a subjective input is indicative of the comfort score of the user. For example, the user can indicate a numerical rating of how comfortable she is. The numerical rating can be measured on a scale of, for example, one to ten, one to twenty, one to thirty, one to one hundred, etc. The numerical rating can be binary, for example, comfortable or uncomfortable, happy or sad, etc. In some implementations, the user device 170 prompts the user to choose between emoticons indicative of the user's comfort, such as a smiley face or a sad face. The smiley face can indicate comfortable, and the sad face can indicate uncomfortable. In some implementations, tests such as ESS, MSLT, PSQI, etc., can capture subjective sleep-related and comfort-related data to inform determination of the comfort score. In some implementations, the test results are adopted as, or as part of, the comfort score.

In some implementations, the comfort score is determined using objective inputs from the one or more sensors 130. Objective inputs from the one or more sensors 130 can be indicative of the comfort level of the user. For example, excessive movement/restlessness of the user during sleep can be indicative of the user being uncomfortable, the user's sympathetic response (e.g., sweating) can be indicative of the user being uncomfortable, the user having a lower sleep quality can be indicative of the user being uncomfortable, etc. Movement and/or restlessness of a user during sleep or while the user is using the respiratory therapy system 120 can be determined using an accelerometer, a SONAR sensor, a RADAR sensor, etc., as described herein. The user's sympathetic response can be temperature detected by a skin thermometer, skin moisture or sweating using galvanic skin response (GSR) sensor, etc. The user's sleep quality can be qualified in terms of duration of sleep, type and duration of sleep stages including awakenings, deep sleep, etc. Some sleep stages may be more beneficial to restfulness (e.g., deep sleep is more beneficial to restfulness than light sleep).

In some implementations, the comfort score is determined using both objective inputs and subjective inputs. Subjective inputs can beneficially fill in gaps in objective inputs to have a more comprehensive view of the comfort level of the user. In some cases, subjective inputs are used to fill in gaps due to absence of or limitations in objective inputs from the one or more sensors 130.

In some implementations, the comfort score can be determined from historic data or can be determined throughout the day. For example, actimetry measured via an accelerometer can be used to infer a user's comfort level during a preceding sleep session. That is, if a user is lethargic, inactive, etc., during the day, the system 100 can infer that the user was uncomfortable during the preceding sleep session. That is, discomfort during the preceding sleep session may be assumed to have contributed to the lethargy. IoT devices and sensors can be employed in this regard to monitor a user's daytime (non-sleep) behavior and correlate the behavior to the preceding night's or nights' sleep and/or comfort data, and compared with historical daytime (non-sleep) behavior and corresponding nights' sleep. IoT devices and sensors can include a smart fridge to monitor food and drink intake, smart TVs to monitor how much TV a user is watching and when the user is watching this TV, smart medicine container/cabinet to monitor medication consumption, etc. Inferring comfort in this manner can help with correcting previous comfort scores or more accurately calculating future comfort scores.

In some implementations, the comfort score is binary and can be trained using a classification algorithm. For example, over a period of time (e.g., over a week, a month, a day, etc.), environmental data can be gathered along with subjective inputs for the environmental data. For example, temperature and humidity can be collected over the period of time, and when the temperature or humidity changes, subjective input can be obtained from the user indicating whether the combination of temperature and humidity is comfortable or uncomfortable. By receiving multiple data points for the environmental data and associating each of the data points with a comfortable-uncomfortable rating, a classification algorithm can be used to divide the environmental data space such that an unknown temperature and humidity combination can be classified as either comfortable or uncomfortable without asking for user input. The classification algorithm being applied to the environmental data space is indicative of the relationship between the environmental data and the comfort score of the user.

Aspects of the present disclosure may be used in place of, for example, a binary comfort score and, for example, the environmental and subjective data, described in the previous example. Although the classification algorithm is described in the previous example in the context of the comfort score being binary, other representations of the comfort score can be used with a classification algorithm. For example, if the comfort score is a value between one to thirty, the classification algorithm can be used to segment comfort scores into one, two, three, four, etc., groups. These groups can be, for example, very comfortable, comfortable, slightly comfortable, neutral, slightly uncomfortable, and uncomfortable. The classification algorithm can be used to segment a continuous value comfort score (or a discrete value comfort score) into any one of these groups.

In the previous example, a classification algorithm was provided as one way of developing the relationship between the comfort score and the environmental data. In some implementations, where the comfort score does not take on a binary value, a regression algorithm can be used to determine the comfort score. For example, if the subjective input is indicative of a comfort score between 1 and 10, the environmental data collected over the period of time can be associated with different comfort scores. For example, {temperature, humidity, comfort score} combinations of {22° C. (~72° F.), 50%, 4}, {23° C. (~73° F.), 30%, 4.5}, {22.5° C. (~72.5° F.), 60%, 5}, {21.5° C. (~70.7° F.), 100%, 8}, {22.8° C. (~73° F.), 55%, 7}, {23° C. (~73° F.), 50%, 6}, {20° C. (~68° F.), 35%, 2} . . . can be obtained over the period of time, and a regression algorithm can be used to obtain a model for estimating comfort scores. For example, the regression algorithm can be used to obtain an equation for determining the comfort scores, such that a {temperature, humidity} combination of {21.8° C. (~71° F.), 78%} can be inserted into the obtained equation to determine the corresponding comfort score.

The classification and regression algorithms described herein can be machine learning algorithms. For example, the classification algorithm can be an unsupervised learning algorithm and the regression algorithm can be a supervised learning algorithm. Temperature and humidity are merely used as examples but other environmental parameters can be included when estimating the comfort score.

In some implementations, physiological data associated with the user informs the comfort score. Examples of physiological data associated with the user includes a respiration signal, a respiration rate, a respiration rate variability, an inspiration amplitude, an expiration amplitude, an inspiration-expiration ratio, a heart rate, a heart rate variability, a blood pressure, a blood pressure variability, pain experienced by user (such as acute pain or chronic pain, including back pain, pain due to bed sores, headaches, or migraines, etc.), movement of the user, a core temperature of the user, muscle tone, brain activity, skin conductance, or any combination thereof. Movement of the user can be an indication of restlessness, which in the context of sleeping, can be interpreted as an indication of discomfort.

In an example, physiological data associated with the user can be obtained over a period of time in order to train a machine learning algorithm. The machine learning algorithm can perform regression or classification as described above. For example, subjective input data used for training the machine learning algorithm can be associated with physiological data. In an example, a data set including {heart rate, blood pressure, skin conductance, comfort score} can be used to train the machine learning algorithm, such that any combination of {heart rate, blood pressure, skin conductance} can be used to estimate the comfort score.

In some implementations, at step 504, a machine learning algorithm is used with the environmental data to estimate the comfort score of the user as previously described. A second machine learning algorithm can be used with the physiological data to check the estimated comfort score. For example, a {temperature, humidity} data set can be used to estimate a first comfort score for the user. A {heart rate, skin conductance} data set can be used to estimate a second comfort score for the user. The first comfort score and the second comfort score can be compared to determine agreement.

In some implementations, the first comfort score can indicate that the user is comfortable but the second comfort score can indicate that the user is not comfortable. The control system 110 can interpret the disagreement between the first comfort score and the second comfort score as a changing preference of the user. In some cases, the user may not be cognizant of the changing preference. In this case, the second comfort score is chosen as the comfort score. In some implementations, the control system 110 can resolve the disagreement between the first comfort score and the second comfort score by combining both first and second comfort scores. For example, the first comfort score can be selected over the second comfort score, the second comfort score can be selected over the first comfort score, the first comfort score and the second comfort score can be averaged, etc.

Step 506 of the method 500 involves adjusting one or more settings of one or more devices (e.g., the devices 190) to improve the comfort score of step 504, based on the relationship determined at stop 504. The one or more settings being adjusted control environmental parameters within the environment of the user. In some implementations, the one or more settings of the one or more devices may be adjusted to maintain the comfort score of step 504, e.g. by reducing the temperature and/or increasing the humidity after the user fell asleep to maintain the comfort score as before the user fell asleep when a higher temperature and/or lower humidity were preferred.

In an example, a temperature of the environment can be adjusted to make the user more comfortable. For example, a {temperature, humidity} data set of {20° C., 35%} can indicate a comfort score of 3, and in order to improve the comfort score to at least 8, the thermostat on an air conditioning unit in the environment can be changed to 22° C. to increase the temperature of the environment to improve the comfort score. Increasing the temperature setting on the thermostat can increase the temperature of the user's environment. The increased temperature in the user's environment can elicit a physiological response from the user. For example, a shivering of the user can be reduced with increased temperature, a heart rate of the user can be reduced with increased temperature, etc.

In some implementations, a noise level and/or pattern of the environment can be adjusted to make the user more comfortable (or to improve or maintain the comfort score of step 504). For example, a noise source (e.g., a television, radio, smart speaker, etc.) can be switched off or its volume can be turned down. In some implementations, a noise level and/or pattern of the environment can be adjusted by masking the noise in the environment. In some implementations, the noise in the environment is masked by playing a sound from the speaker 142. The played sound can include white noise, pink noise, brown noise, or any other soothing sounds such as beach sounds, bird sounds, waterfall sounds, running water sounds, wind sounds, etc. The played sound can be played at an adjusted volume based on the comfort score such that the volume can be increased or decreased based on the played sound's effect on the comfort score. In some implementations, the noise level and/or pattern of the environment is adjusted by adjusting respiratory therapy device settings (e.g., to reduce motor speed and associated noise), introducing noise cancellation (e.g., in the environment in which the user is located, within earphones worn by the user, etc.).

In some implementations, an adjustable bed or an adjustable (e.g., smart) pillow and/or mattress can be adapted to make the user more comfortable. For example, the one or more sensors 130 can detect a user's mouth leak (based on e.g., acoustic and/or flow signals) and adjust settings of the adjustable bed or the adjustable pillow and/or mattress. The adjusted settings can be made to promote moving the user to a position that encourages closure of the user's mouth, less mouth leak, etc. In some implementations, humidification settings of the respiratory therapy system 120 and/or the bedroom are adjusted when mouth leak is detected since increased humification may result in less discomfort due to a dry mouth (or portion of mouth, e.g., tongue and/or lips) caused by the mouth leak.

In some implementations, a comfort score associated with environmental data can be determined, and a comfort score associated with physiological data can be determined, as previously discussed. Both comfort scores can be monitored to verify effect of adjusting the one or more settings on the devices 190.

In some implementations, to determine which of the one or more settings to adjust, a baseline is established for each metric in the physiological data. For example, a {heart rate, skin conductance, core temperature} data set can be obtained for the user such that normal values for each of the metrics in the data set is determined. When a measurement indicates that any one of the metrics in the {heart rate, skin conductance, core temperature} data set is not within the established baseline, then the comfort score can be determined as being inversely proportional to the amount of deviation. If the baseline of {heart rate, skin conductance, core temperature} were {70 beats per minute, 0.0001 Ohms$^{-1}$, 36.5° C. (~98° F.)}, then obtaining values of {70 beats per minute, 0.001 Ohms$^{-1}$, 36° C. (~97° F.)} can indicate that the user is uncomfortable. The comfort score can be determined based on the skin conductance being an order of magnitude off from the baseline. Thus, a baseline comfort score can be reduced in proportion to the skin conductance being an order of magnitude off from the baseline. In some implementations, the baseline comfort score is inversely proportional to the amount of deviation. In some implementations, a threshold is set such that the 36° C. temperature being within the threshold indicates that the user is within the baseline value for the core temperature such that the baseline comfort score is not affected by the core temperature measurement.

In some implementations, a look up table is used to determine which of the devices 190 to adjust. In some cases, the look up table is organized as having target physiological metrics (e.g., heart rate, heart rate variability, core temperature, skin conductance, blood oxygen level, blood pressure, blood pressure variability, movement of the user, etc.) coupled with one or more of the devices 190. For example, in the case of an adjustment for reducing or increasing core temperature of the user, an air conditioning or a fan system can be engaged. The user can be prompted via the user device 170 to turn on or turn off, or otherwise adjust the settings of, the air conditioner or fan. The control system 110 can automatically set the thermostat for the air conditioning unit. In another example, to correct for excessive light in an environment, the control system 110 can instruct the user to close blinds or can automatically close the blinds. In another example, to correct for not having enough light in an environment, the control system 110 can automatically turn on lights in the environment. In some cases, depending on the time of day, the control system 110 can instruct opening of blinds to get natural light. In some cases, the control system 110 can instruct opening of the blinds to get natural light based on a health condition associated with the user, a health condition associated with a partner of the user, a health condition associated with a pet of the user, or any combination thereof.

In some implementations, volume of music or other media, such as television, in the environment can be adjusted based on preferences of the user. For example, if the user does not usually play loud music, then a decibel level of music can be learned by the control system 110 for the user. The control system 110 can adjust the decibel level to make the user more comfortable. Sensing sound in the background along with an elevated heart rate can be used to determine that the background volume level may be too high. The user device 170 can prompt the user to increase or decrease the volume in some implementations, or the control system 110 can automatically increase or decrease the volume in other implementations.

In some implementations, soothing sounds are played by the speaker 142 to make the user more comfortable. For example, if the user's physiological data indicates that the user's heart rate is elevated, and the motion sensor 138 indicates that the user is moving more than usual (e.g., using a deviation from the baseline or using a machine learning algorithm), then the control system 110 can determine that the user is uncomfortable. The speaker 142 can play soothing sounds (e.g., white noise, calming music, a favorite music artist of the user, etc.) to improve comfort level of the user. In some instances, the control system 110 can determine using the microphone 140 that there is a background noise and can play soothing sounds to drown out the background noise in order to bring the user's physiological metrics to baseline or other desired level.

Figure 6:
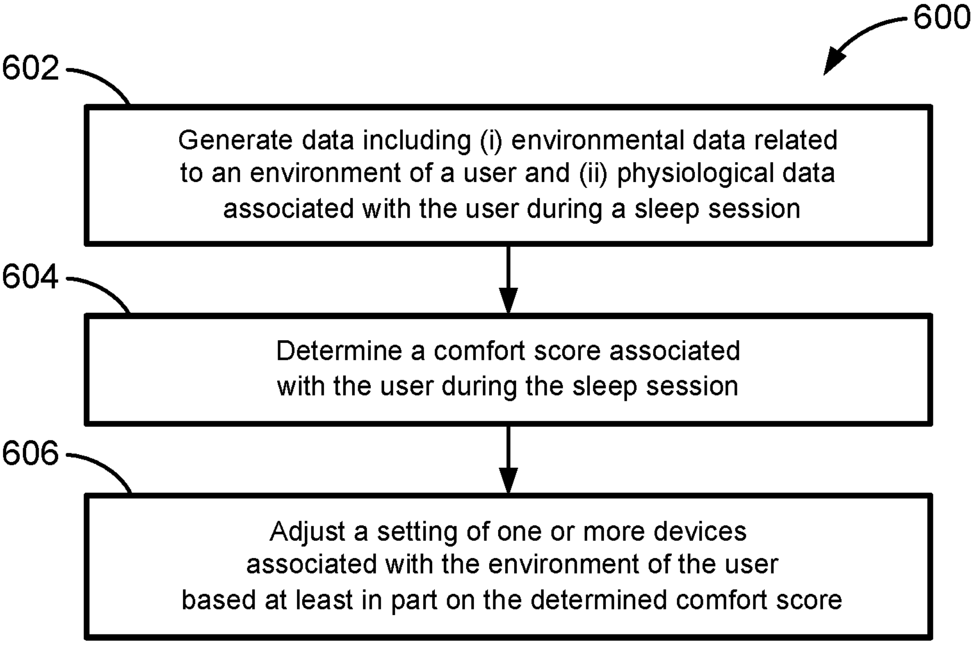
FIG. 6 is a process flow diagram for a method for modifying an environment of a user during a sleep session, according to some implementations of the present disclosure.

Adjusting the user's environment to improve a comfort level of the user can be combined with therapies for addressing one or more disorders that the user is suffering from. For example, the user may use the respiratory therapy system 120 of FIG. 1 to treat a respiratory and/or sleep disorder. Referring to FIG. 6, a method 600 for modifying an environment of the user during a sleep session is provided. The steps in the method 600 can be performed using the system 100.

Step 602 of the method 600 involves generating data including (i) environmental data related to an environment of a user and (ii) physiological data associated with the user during a sleep session. The environmental data and the physiological data can be generated from the sensors 130 as discussed above. Examples of the environmental data include a temperature of the environment of the user, a humidity of the environment of the user, a luminosity of the environment of the user, a noise level in the environment of the user, a noise pattern in the environment of the user, or any combination thereof. Examples of physiological data include a respiration signal, a respiration rate, a respiration rate variability, an inspiration amplitude, an expiration amplitude, an inspiration-expiration ratio, a number of events per hour, a pattern of events, a duration of each of the events, a heart rate, a heart rate variability, a blood pressure, a blood pressure variability, movement of the user, sleep efficiency, therapy efficacy, a core temperature of the user, a sleep stage, residual AHI, a duration of the sleep session that the user is on-therapy, a duration of the sleep session that the user is off-therapy, sleep onset, muscle tone, brain activity, skin conductance, sleep cycle, or any combination thereof.

In some implementations, the data is generated from at least one or more of the sensors 130. The sensors 130 can be integrated in the respiratory therapy system 120, the user device 170, the activity tracker 180, and/or the devices 190. In some implementations, the devices 190 includes the respiratory therapy system 120, the user device 170, and/or the activity tracker 180. In an example where the user is using the respiratory therapy system 120 during at least a portion of the sleep session, one or more of the sensors 130 embedded in the respiratory therapy system 120 can be used to determine humidity of supplied pressurized air to the airway of the user, a respiration signal for the user, a respiration rate for the user, an inspiration amplitude for the user, an expiration amplitude for the user, etc. Conditions for the supplied pressurized air in the user interface 124, or the conduit 126 can be determined using the sensors 130. For example, temperature and/or humidity of the supplied pressurized air within the conduit 126 can be different from humidity and/or temperature within the bedroom of the user. In some implementations, a portable oxygen concentration system is connected to the respiratory therapy system 120 such that the respiratory therapy system 120 is able to supply oxygen to the user. That is, the respiratory therapy system 120 can adjust oxygen concentration of the supplied pressurized air within the conduit 126 such that the oxygen concentration of the supplied pressurized air is different from the oxygen concentration within the bedroom of the user.

Step 604 of the method 600 involves determining a comfort score associated with the user during the sleep session. The comfort score associated with the user can be determined based at least in part on the physiological data and/or the environmental data obtained at step 602. The comfort score is indicative of a comfort level of the user during at least a portion of the sleep session. The comfort score can be determined in any manner as discussed above in connection with step 504 of the method 500.

In some implementations, the generated data at step 602 includes a number of events per hour, a pattern of the events, a duration of each of the events, or any combination thereof. Examples of events include central apneas, obstructive apneas, mixed apneas, hypopneas, snoring, periodic limb movement, awakenings, chokings, epileptic episodes, seizures, or any combination thereof. The flow rate sensor 134 can be used to measure snoring oscillation. In an example, the comfort score can be determined based on baseline values for the number of events per hour, the pattern of the events, the duration of each of the events, etc. A look up table can be used to determine the comfort score. For example, starting from a baseline comfort score, based on the number of events per hour exceeding a threshold of events per hour, the comfort score can be determined to be the baseline comfort score adjusted by a factor obtained from the look up table. If the baseline comfort score is 8/10 and there is a threshold of 3 events per hour, then if the number of events per hour is determined to be 5, then the comfort score can be determined to be 7 based at least in part on the decreasing the baseline comfort score by a factor of 0.5 for each event per hour exceeding the threshold of events per hour.

Different sensors in the one or more sensors 130 can complement and synergize with each other to produce a holistic view of the user's comfort. For example, discomfort manifested as apnea events may be measured in terms of an AHI and based on sensor data from the flow and pressure sensors of a respiratory therapy device 122, but an Oxygen Desaturation Index (ODI) measured using an SpO2 sensor may detect discomfort related to oxygen desaturations. The ODI measurement may be used to (i) confirm the AHI score or (ii) independently verify user discomfort even though the ODI measurement (e.g., one or more oxygen desaturations) may not have been detected or categorized as apnea events that contribute to the AHI score. Thus, a combination of different sensors can produce a more holistic view of a user's comfort. Settings of the respiratory therapy system 120 can then be adjusted appropriately (e.g., at step 606 below). For example, auto-adjustment features of respiratory therapy devices, e.g., the "Autoset" and "Autoset for Her" features of RESMED PAP devices can auto-adjust airflow pressure to improve comfort.

In some implementations, a machine learning algorithm or model is trained using training data that includes previously acquired measurements. For example, a regression and/or a classification algorithm can be used to determine the comfort score as discussed in connection with step 504 of FIG. 5. The training data can include physiological data, environmental data, or both. Thus, a combination of physiological data, a combination of environmental data, or both can be related to comfort scores, such that any measured values or combinations of the physiological data and/or the environmental data can be provided, as input, to the trained machine learning model. The trained machine learning model should then provide, as output, estimated comfort scores.

In some implementations, the training data for training the machine learning model includes measurements acquired in historical sleep sessions before a current sleep session for which a comfort score is being determined. Historical sleep sessions are previous sleep sessions of the user prior to the current sleep session. The historical sleep sessions can be associated with one or more historical comfort scores, historical physiological data, historical environmental data, etc. For example, over a period of time (e.g., a week, two weeks, a month, etc.), historical sleep session data including historical physiological data and historical environmental data can be used to train the machine learning model.

Historical comfort scores associated with the historical sleep sessions can be developed over the period of time, such that over the period of time, later obtained historical comfort scores can better track the comfort levels of the user.

In some implementations, the training data for training the machine learning model includes measurements acquired in historical sleep sessions of other individuals. For example, historical sleep session data and historical comfort scores from other individuals, not including the user, can be used to train the machine learning model. When other individuals' historical sleep session data and historical comfort scores are used in training the machine learning model, the trained machine learning model will capture or reflect comfort levels for an average person. Modeling the average person can be beneficial because a comfort level modeling for the average person can be readily assumed for new users of the system 100 who have not provided any information to the system 100.

In some implementations, the individuals can be separated into cohorts, such that, for each cohort, the control system 110 can train a machine learning model that captures or reflects comfort levels for an average person in the cohort. The cohort can be based at least in part on demographic information of the average person in the cohort, health condition of the average person in the cohort, a blood type of the average person in the cohort, a body mass index (BMI) of the average person in the cohort, a resting heart rate of the average person in the cohort, a fitness status of the average person in the cohort, or any combination thereof. A user's blood type can impact metabolism of the user which can influence temperature regulation mechanisms of the user's body. The fitness status can include aerobic fitness status, muscular strength and endurance status, body composition (e.g., waist circumference, height, fat percentage, etc.), or any combination thereof. The health condition can include diabetes, high blood pressure, insomnia, general circulatory illness, asthma, chronic obstructive pulmonary disease (COPD), arthritis, spinal cord injury, pain experienced by user (such as acute pain or chronic pain, including back pain, pain due to bed sores, headaches, or migraines, etc.), stroke, hyperthyroidism, cardiovascular health condition, or any combination thereof. Cardiovascular health condition includes, for example, stroke, heart failure, hypertensive heart disease, rheumatic heart disease, cardiomyopathy, abnormal heart rhythms, congenital heart disease, valvular heart disease, carditis, aortic aneurysms, peripheral artery disease, thromboembolic disease, venous thrombosis, etc.

In some implementations, when the machine learning model is trained using historical sleep session data, the machine learning model can be improved over time by successively training the machine learning model with data generated at step 602. For example, the user of the system 100 can start with a trained machine learning model for the average person. Over use of the system 100, the machine learning model is successively trained with generated data associated with the user. As such, over time, the machine learning model can shift from merely modeling the average person to including preferences applicable to a specific user. In some implementations, successively training the machine learning model includes tuning certain parameters based on preferences of the specific user.

By using a machine learning model to determine comfort levels of the specific user, latent preferences of the specific user can be determined without having the user inform the system 100 of specific preferences. For example, certain combinations of physiological data and/or environmental data generated by the sensors 130 can be used to determine that the user is comfortable based on the user not having a physiological response to the environment. For example, the user can be in a 27° C. (~80° F.) room and the sensors 130 generate a stable heartrate, lower than 0.001 $Ohm^{-1}$ conductance indicating that the user is not sweating, etc. Although the user did not specify that 27° C. (~80° F.) is a comfortable temperature, the control system 110 can determine over time, based on the physiological response of the user to the temperature, that the comfort score for the user is about an 8.5/10. Latent preferences can be determined relative to threshold values, for example, humidity not being above a humidity threshold or being above a humidity threshold, temperature not being above a temperature threshold or being above the temperature threshold, etc. An example of a latent preference can be that the user prefers a room temperature of about 22° C. (~72° F.) when humidity is below 25%. Thus, changing only temperature without consideration of humidity may not satisfactorily meet an acceptable comfort level for the user.

In some implementations, user profiles can be used to track and store parameters of trained machine learning models for easy retrieval. For example, a profile of the user can be stored in the memory device 114. The profile of the user can include demographic information associated with the user, health information associated with the user, or any other information that can be used to group the user in a cohort, as previously discussed. The profile of the user can include parameters of the trained machine learning models including regression coefficients for modeling the comfort score of the user.

In some implementations, the stored parameters of trained machine learning models in different user profiles can be used to develop or train a general machine learning model for an average person. For example, user profiles of a plurality of users can include different regression coefficients for different physiological metrics and/or different environmental conditions. To obtain the general machine learning model, statistical methods (e.g., mode, average, median, etc.) can be applied to the different regression coefficients to obtain regression coefficients for the general machine learning model. For example, for the tuple {heartrate, temperature, humidity}, if profile of individual 1 has regression coefficients {−0.02, 0.3, 0.001}, profile of individual 2 has regression coefficients {0.01, 0.4, 0.003}, and profile of individual 3 has regression coefficients {0.02, 0.1, 0.001}, then regression coefficients for the general machine learning model can be chosen, for example, as an average of the regression coefficients (i.e., {0.003, 0.26, 0.002}). Thus, instead of storing underlying data that was used to generate the different regression coefficients for the different individuals in order to generate the general machine learning model, the parameters of each individual's trained machine learning model can be used to adjust and/or train the general machine learning model. This approach utilizes storage space more efficiently, and as each individual's model parameters change over time, the general machine learning model can change as well. The general machine learning model is used to express comfort level for the average person. As discussed above, machine learning models based on cohorts can be developed in a similar manner by using information from individuals in a same cohort, however that cohort is defined.

Step 606 of the method 600 includes adjusting a setting of one or more devices 190 associated with the environment of the user based at least in part on the determined comfort score at step 604. In some implementations, the one or more devices 190 includes the respiratory therapy system 120, such that, one or more settings of the respiratory therapy system 120 are adjusted based on the comfort score. Examples of settings that can be adjusted include adjusting a temperature setting for the environment of the user, a humidity setting for the environment of the user, a luminosity setting for the environment of the user, a humidification setting of the respiratory therapy system 120, a temperature (e.g., airflow temperature) setting of the respiratory therapy system 120, a pressure setting of the respiratory therapy system 120, or any combination thereof.

In some implementations, the setting of the one or more devices 190 are adjusted during the sleep session. For example, the control system 110 determines a comfort score of 4/10 for the user based on receiving intermittent street noise over a two-hour period while the user is asleep. The control system 110 can cause the speaker 142 to play soothing sounds and/or white noise to drown out the street noise for the remainder of the sleep session. In some implementations, an adjustable bed and/or pillow is adjusted during the sleep session to alleviate the control system 110 determining that the user is experiencing pain, with the determined experienced pain contributing to a low comfort score.

In some implementations, the setting of the one or more devices 190 are adjusted during the sleep session during certain sleep stages, during which the adjustments are less likely to wake the user. For example, the control system 110 determines that the setting of the one or more devices 190 should be adjusted. The control system 110 then determines the sleep stage of the user. In some implementations, it is difficult to wake the user in deep sleep stage, somewhat less during REM sleep stage, and quite easily during light sleep. Thus, before making any adjustment that might wake the user (e.g., changing a pressure setting of the respiratory therapy system 120), the control system 110 determines whether the user is in a sleep stage which the chances of waking are less likely. For example, if the user is in deep sleep, then the control system 110 can proceed with adjusting the setting, but if the user is in light sleep, then the control system 110 can wait for the user to enter the REM sleep stage or the deep sleep stage.

In some implementations, the setting of the one or more devices 190 are adjusted after the sleep session but prior to a next or subsequent sleep session. For example, a lux meter in the sensors 130 captures 1 lux of luminous flux within the bedroom of the user while the user is asleep, and the control system 110 determines a comfort score of 5/10 for the user. The control system 110 determines that the bedroom lights are off, but the only way to reduce the luminous flux captured within the bedroom of the user is to lower the blinds. The control system 110 waits till a subsequent sleep session to lower the blinds. In some cases, lowering the blinds may cause noise that can further disturb the user's sleep, thus, waiting for the subsequent sleep session is preferable. The control system 110 can estimate an amount of noise that can be caused and estimate effect of that noise as a projected comfort score. If the projected comfort score is lower than the determined comfort score, the control system 110 can adjust the settings of the blinds prior to the subsequent sleep session rather than during the current sleep session. In some implementations, the setting of the one or more devices 190 are adjusted during the subsequent sleep session. For example, the user may prefer the blinds open while awake, thus the control system 110 first determines that the user is asleep before adjusting the settings for the blinds.

In some implementations, the setting of the one or more devices 190 is adjusted based at least in part on a time of day, a season during the year, demographic data, user inputs, a duration of the sleep session, a point in time during the sleep session, a sleep state of the user, a sleep stage of the user, or any combination thereof. For example, if the user is sleeping during the day, then brightness within the environment of the user (e.g., the bedroom in which the user is sleeping) can be deduced to be a controlling factor in the determined comfort score. Thus, adjusting blinds to reduce the amount of light in the environment can be performed before any other adjustments. In another example, adjusting blinds or adjusting one or more of the devices 190 that can cause excess sounds to be produced may be performed in the beginning of the sleep session rather than the middle or the end of the sleep session. In some cases, adjusting one or more of the devices 190 that can cause excess sounds to be produced can be performed minutes, 7 minutes, 10 minutes, an hour, etc., into the sleep session.

In an example, adjusting one or more of the devices 190 is based on a sleep state and/or a sleep stage of the user. In some cases, if the control system 110 determines that the user is light sleep stage, then adjustments are delayed until the user enters a deep sleep stage. The control system 110 can delay causing the adjustments based on the user being more prone to wake up in the light sleep stage. In some implementations, the control system 110 can cause the adjustments be made during the light sleep session if the control system 110 determines that the user is about to wake up. The control system 110 can determine the user is about to wake up based on a waking pattern of the user, an alarm of the user sounding, etc. The control system 110 can adjust settings on the one or more devices 190 in anticipation of the user's preference changing. For example, the user may prefer a bedroom temperature of 18° C. (~65° F.) when asleep and a bedroom temperature of 22° C. (~72° F.) when awake. In some implementations, the user may acclimate to different seasons throughout the year. The control system 110 can adjust the settings based on seasonal acclimation. For example, the control system 110 can set a temperature of 22° C. (~72° F.) during the summer and a temperature of ° C. (~78° F.) during the winter.

Season, time of day, sleep stage, sleep state, or other examples are used herein as examples. These factors can be incorporated in the environmental data and/or the physiological data, and can therefore be captured within the comfort score determined in step 604. For example, same environmental conditions {temperature, humidity} in the summer can yield a different comfort score than in the winter because the model used to determine the comfort score can take into account seasonal parameters like summer and winter. In some implementations, where a machine learning model is used, time of day or season may not have an impact on the comfort score, given similar environmental conditions.

In some implementations, the adjustment of the settings of one or more of the devices 190 is based on user inputs. The user inputs can be collected using the user device 170 or the display device 128 of the respiratory therapy system 120. The user inputs can include fatigue, wakefulness, health conditions associated with the user, health conditions associated with a partner of the user, health conditions associated with a pet of the user, or any combination thereof. For example, if the user is suffering from a cold, then a previously comfortable temperature of 22° C. (~72° F.) may be less desirable than a temperature of 25.5° C. (77° F.). In some cases, based on a pet of the user and/or a partner of the user (e.g., the bed partner 220 of FIG. 2) being in the same room as the user, the control system 110 can consider the comfort level of the pet and/or the bed partner when adjusting settings of the one or more devices 190. An aggregated comfort score can be used to determine whether an adjustment should be made. In some implementations, the aggregated comfort score is provided by an aggregated machine learning model determined using individual machine learning models as discussed earlier. For example, parameters for a machine learning model for the user can be combined with parameters for a machine learning model for the partner of the user to obtain parameters for the aggregated machine learning model.

Although fatigue, wakefulness, health conditions associated with the user, health conditions associated with a partner of the user, and health conditions associated with a pet of the user are described as user inputs, in some implementations, these items can be automatically determined by the control system 110 using the sensors 130. For example, the microphone 140 can capture a frequency of the user sneezing or coughing and deduce that the user has a cold or allergies (e.g., allergic rhinitis due to pollen, dust mites, animal skin or saliva particles, etc.). The physiological determination of a cold or allergies can affect the comfort score determined at step 604 such that the adjustment at step 606 is also influenced. For example, sneezing or coughing are physiological responses that can reduce the comfort score of the user, prompting the control system 110 to cause, for example, a fan in the environment of the user to turn on to promote air circulation. Similarly, other health conditions (e.g., flu, fever, etc.) can be detected using the sensors 130 (such as temperature sensor 136), including sensors of the respiratory therapy system 120, the user device 170, and/or the activity tracker 180. Signatures of the health conditions can be identified by the control system 110 in order to determine the comfort score and determine how to adjust the devices 190 to improve the determined comfort score.

In some implementations, status of fatigue is inferred from heart rate variability, changes in gait/activity levels, or physiognomy changes in the user. Heart rate variability and activity levels can be determined using wearable devices (e.g., a smartwatch, fitness tracker, smart phone, etc.). Physiognomy changes can be used to infer fatigue as a result of image analysis. A psychomotor vigilance test (PVT) can be used to determine fatigue by evaluating reaction times and hand/eye coordination. PVT tests are a reasonable indicator of sleepiness which is correlated with fatigue. In some implementations, EEG measurements are used to determine fatigue. WO 2015/054134, which is incorporated by reference, includes multiple ways of determining fatigue.

In some implementations, settings for the one or more devices 190 is stored in a profile of a user. For example, the profile of the user can include a temperature setting for a thermostat that controls an air conditioning unit, at least one name of an audio file (e.g., music, white noise, nature sounds, soothing sounds, etc.) that can be played to drown out noise in the user's environment, whether to use an audio file to drown out noise, a volume that the audio file should be played, a humidification setting for air supplied by the respiratory therapy system 120, a fan speed setting for a fan, a temperature setting for a heated blanket, a setting for an adjustable bed frame on whether barriers are raised to prevent the user from falling out of bed, a massage speed for a massage system (e.g., a chair massager), a network name or identification for a mobile device or app associated with the user, a network name or identification for an activity tracker device associated with the user, etc.

In some implementations, settings for the one or more devices 190 when adjusted, replaces a historical setting of the one or more devices 190 in the profile of the user. For example, the control system 110 determines that during winter, the user historically preferred a 24° C. (~75° F.) setting on her thermostat. This winter, however, the control system 110 determines that the thermostat should be set to 21° C. (~70° F.). The new setting of 21° C. (~70° F.) can override the previous 24° C. (~75° F.) setting in the profile of the user. In some implementations, default settings are available for the user based on historical data, including historical settings from one or more individuals. The historical data can include historical sleep session data associated with the one or more individuals.

In some implementations, transient health conditions like allergies, flu, cold, etc., can influence a profile of the user. For example, the control system 110 determining that the user has a transient health condition, can import settings from an average person in a cohort that matches the transient health condition that the user is suffering from. The imported settings can be used and refined while the user suffers from the transient health condition. Once the transient health condition is no longer present, the user's profile can revert back to the user's personalized settings prior to when the transient health condition was detected.

In some implementations, the control system 110 can use regional weather/pollen information to determine air quality conditions. The control system 110 can determine whether the air quality conditions will trigger an allergic reaction from the user or whether the air quality conditions are contributing to a lower comfort score for the user. The control system 110 can cause an air filtration system (e.g., an air filter, an air cleaner, an air purifier, etc.) to turn on. In some implementations, the control system 110 can adjust a setting of the air filtration system (e.g., cause a fan of the air filtration system to change from a first fan speed to a second fan speed, where the second fan speed is greater than the first fan speed). The control system 110 can cause windows in the home of the user to close based at least in part on weather and/or pollen information obtained over a network (e.g., the Internet).

In some implementations, default settings can be obtained from a look up table. The look up table can associate each default setting with a default comfort score. In some implementations, the look up table provides an average comfort score for each combination of settings associated with individuals who have previously used the combination of settings. At step 606, the default comfort score for a combination of settings can be compared with the determined comfort score of step 604. If the determined comfort score is less than the default comfort score, then the setting of the devices 190 can be adjusted to match the combination of settings that provides the default comfort score.

The default settings, default comfort scores, etc., can be subject to cohorts as described above in connection with user profiles and is not repeated here. For example, default settings for an average person with arthritis can be different from default settings for an average person with asthma. Default settings for an average Texan can be different from default settings for an average Michigander.

In some implementations, adjustments to the settings of the one or more devices, such as settings of the respiratory therapy system 120 and/or the environment of the user, are transferable. That is, the settings may be learned and stored, and applied to a new respiratory therapy system (e.g., a new or temporary PAP device) and/or a new environment of the user. An example of a temporary PAP device is a travel PAP device, and an example of a new environment of the user is a hotel room.

In some implementations, adjustment to environmental settings can take into account that an environment may be shared with another individual, e.g., a bed partner of the user. Therefore, adjustment of settings may apply to only the user's environment, e.g., turning off a light on the user's side of the bed, adjusting a temperature of an electric blanket used by the user or a portion of an electric blanket for warming or cooling a user and shared by the user with a bed partner, etc. The adjustments may be made based on proximity sensors when the system 100 is unsure of the user's environment vs. the bed partner's environment. Devices more proximate to the user can be determined to be associated to the user and can be adjusted accordingly, while devices more proximate to the bed partner can be left unadjusted. Proximity can be determined by a proximity sensor (e.g., using RADAR sensor, SONAR sensor, LiDAR sensor, etc.). Identification of the user, bed partner, etc. may be determined based on a detected biometric signature, for example, as described in US2018/0106897 which is hereby incorporated by reference herein in its entirety. The biometric signature may be on characteristic respiratory, cardiac, acoustic (e.g., vocal) and/or movement (e.g., gait) parameters and may be used to distinguish the user and from the bed partner and/or other individuals in the environment. The adjustments may be made based on the user's profile where devices associated with the user are identified in the user's profile. As such, the system 100 does not guess based on proximity. The system 100 may also access physiological data of the another individual, e.g., a bed partner, and either adjust their environment and/or monitor the effect of the adjustment of the user's environment and balance any detrimental effects on the other individual's discomfort.

The methods 500 and 600 of FIGS. 5 and 6, respectively, can be performed multiple times. That is, step 506 can loop back to step 502, and step 606 can loop back to step 602. That way, the comfort score can be updated over a period of time, and the environmental conditions can continually be changed using the devices 190 in order to maintain or enhance comfort levels of the user. In an example, the method 600 can be performed repeatedly throughout the sleep session such that a most recently updated comfort score is used to adjust the setting of the one or more devices.

In some implementations, the system 100 supports a platform such that when a new user joins the platform, the system 100 proposes an expected comfort profile for the new user based on normative comfort settings accumulated over time from a plurality of individual profiles for individuals that have already used the platform. These normative comfort settings can be selected based on user personal information (e.g., demographic information, health information, etc.). Over time, the initial comfort profile that was provided to the user is refined as physiological data, comfort scores, and/or environmental data associated with the user accumulates. The refined comfort profile can be used by the system 100 to help the user have a better quality of sleep. For example, the control system 110 can adjust settings in the environment of the user based on the refined comfort profile to change the environment of the user to match known and/or unknown preferences of the user.

In some implementations, the refined comfort profile of the user can be fed back to the global database to adjust and/or refine the normative comfort settings. That way, first time experiences of new incoming users are improved. In some implementations, medical issues, health conditions, etc., are taken into consideration when determining the normative comfort settings. In some implementations, normative comfort settings can be fed back to individual user profiles for current users to better personalize the individual user profiles.

In an example, the bins used for defining user classes (or cohorts) can be refined as the database of users becomes larger and more user phenotypes (or distinguishing features) are determined. One might start initially with the typical phenotypes (e.g., gender, body mass index, age) and progressively add more variables (e.g., health history, etc.) as more data becomes available. The process to add new variables can be based for instance on a machine learning algorithm (e.g., a clustering algorithm). For example, given a large number of personalized settings and also meta-data regarding a large number of users, the clustering algorithm can be used across dimensions of the meta-data surrounding the users. The meta-data can include new variables (e.g., health history, blood type, etc.), but prior to the clustering algorithm, the control system 110 is not sure which variables may be relevant. After the clustering algorithm is run, the control system 110 can develop insights regarding new variables that can be relevant. In some implementations, the personalized settings profiles can be grouped in clusters based on some similarity metric—and then work backwards to deduce what are the meta-data classes that are mostly associated with these clusters. For new incoming (or new) users, a best guess settings combinations is selected based solely on their meta-data.

In some implementations, the system 100 allows controlling the devices 190 based on sleep stage. For example, when a user is in REM sleep, a temperature of the room can be set to a first value, but when the user is in non-REM sleep, the temperature of the room can be set to a second value which is different from the first value. In some implementations, pressure and/or humidification settings on the respiratory therapy system 120 is adjusted based on sleep stage. For example, a first set of AHI values can result in a first comfort score. If the first comfort score is below a threshold, then the settings of the respiratory therapy system 120 can be adjusted to obtain a second comfort score that is higher than the first comfort score. In this example, the sleep of the user can be monitored, without input from the user, and quality of sleep can be improved due to improved comfort level of the user.

In some implementations, progression of sleep stages can be used to determine comfort score. For example, light sleep stage can transition to deep sleep stage then to REM sleep stage, with each having a different duration throughout the time the user is asleep. Longer deep sleep stages are usually present in the beginning of the sleep session, and longer REM sleep stages are usually present at the end of the sleep session. The control system 110 can track duration of each sleep stage as well as progression between sleep stages in order to determine the comfort score.

In some implementations, improved sleep quality and comfort scores can be provided to the user via the user device 170 so that the user can track her sleep quality. The determined comfort score can be provided to the user prior to the user falling asleep (e.g., at bed time $t_{bed}$ of FIG. 4). The message provided to the user can include "Please use the respiratory therapy system to maintain this comfort score throughout the night." In some implementations, the comfort score can be provided to the user at time $t_{rise}$ of FIG. 4 if the user did not use the respiratory therapy system 120 during the sleep session. An example message of "Please use the respiratory therapy system next time to improve your comfort score while you are asleep."

Although steps 502 of FIG. 5 and 602 of FIG. 6 are described separately above, activities involved in generating environmental data in step 502 can apply to step 602, and vice versa. Similarly, although steps 504 and 604 are described separately above, activities involved in determining a comfort score in step 504 can apply to step 604, and vice versa. Lastly, although steps 506 and 606 are described separately, activities involved in adjusting settings of one or more devices in step 506 can apply to step 606, and vice versa.

One or more elements or aspects or steps, or any portion (s) thereof, from one or more of any of the claims below can be combined with one or more elements or aspects or steps, or any portion(s) thereof, from one or more of any of the other claims below, to form one or more additional implementations and/or claims of the present disclosure.

While the present disclosure has been described with reference to one or more particular embodiments or implementations, those skilled in the art will recognize that many changes may be made thereto without departing from the spirit and scope of the present disclosure. Each of these implementations and obvious variations thereof is contemplated as falling within the spirit and scope of the present disclosure. It is also contemplated that additional implementations according to aspects of the present disclosure may combine any number of features from any of the implementations described herein.

What is claimed is:

1. A method comprising:

generating, using one or more sensors, first data, the first data including (i) first environmental data related to an environment of a user and (ii) first physiological data associated with the user during a sleep session;

establishing a baseline for at least one metric in the first physiological data;

based at least in part on the first physiological data, determining a first comfort score associated with the user during the sleep session;

based at least in part on the environmental data, determining a second comfort score associated with the user during the sleep session, the first and second comfort scores being inversely proportional to an amount of deviation from the baseline and being indicative of a comfort level of the user during at least a portion of the sleep session;

determining a representative comfort score that represents the comfort level of the user by selecting one of the determined first comfort score or the determined second comfort score based at least in part on a comparison of the determined first comfort score and the determined second comfort score; and based at least in part on the determined representative comfort score, adjusting a setting of one or more devices associated with the environment of the user.

2. The method of claim 1, wherein the setting of the one or more devices is stored in a profile of the user, wherein the adjusted setting of the one or more devices replaces a historical setting of the one or more devices in the profile of the user, and wherein the historical setting of the one or more devices is a default setting selected for the user based at least in part on historical sleep-session data associated with at least one person during one or more historical sleep sessions, the historical sleep-session data including historical physiological data associated with the at least one person and historical environmental data associated with the at least one person.

3. The method of claim 2, wherein the determining the first comfort score or determining the second comfort score includes:

determining the first comfort score using a machine learning model that takes as input the first physiological data and provides as output the first comfort score, wherein the machine learning model is trained using (i) the historical sleep-session data associated with the at least one person and (ii) historical comfort scores associated with the at least one person; and successively training the machine learning model based at least in part on the generated first data, the determined first comfort score, or both.

4. The method of claim 3, wherein the successively trained machine learning model is used to determine latent preferences of the user, wherein the determined latent preferences include a room temperature being below a temperature threshold or the room temperature being above the temperature threshold, a room humidity being below a humidity threshold or the room humidity being above the humidity threshold, or any combination thereof.

5. A method comprising:

generating physiological data associated with a user, the physiological data comprising one or more metrics;

determining a comfort score of a user based at least in part on the generated physiological data by:

establishing a baseline for each metric in the physiological data;

determining whether any of the metrics in the physiological data deviates a threshold amount from the established baselines; and based on the any of the metrics deviating from the threshold amount, determining the comfort score, the comfort score being inversely proportional to an amount of deviation and being indicative of a comfort level of the user;

generating environmental data related to an environment of the user;

analyzing the environmental data to determine a relationship between one or more environmental parameters within the environmental data and the comfort score of the user, the one or more environmental parameters being controlled by one or more devices; and adjusting one or more settings of the one or more devices based on the relationship to improve the comfort score of the user.

6. The method of claim 5, wherein the adjusting the one or more settings of the one or more devices involves adjusting a first set of devices in the one or more devices, the first set of devices being devices that are proximate to the user as determined by a proximity sensor.

7. The method of claim 5, wherein the adjusting the one or more settings of the one or more devices involves adjusting a second set of devices in the one or more devices, the second set of devices being devices that are identified in a user profile associated with the user.

8. A system for improving or maintaining a comfort level of a user, comprising:

a sensor configured to generate first data, the first data including (i) first environmental data related to an environment of a user and (ii) first physiological data associated with the user during a sleep session;

one or more devices associated with the environment of the user;

a memory storing machine-readable instructions; and a control system including one or more processors configured to execute the machine-readable instructions to:

establish a baseline for at least one metric in the first physiological data;

based at least in part on the first physiological data, determine a first comfort score associated with the user during the sleep session;

based at least in part on the environmental data, determine a second comfort score associated with the user during the sleep session, the first and second comfort scores being inversely proportional to an amount of deviation from the baseline and being indicative of a comfort level of the user during at least a portion of the sleep session;

determine a representative comfort score that represents the comfort level of the user by selecting one of the determined first comfort score or the determined second comfort score based at least in part on a comparison of the determined first comfort score and the determined second comfort score; and based at least in part on the determined representative comfort score, adjust a setting of the one or more devices associated with the environment of the user.

9. The system of claim 8, wherein the sensor is further configured to generate second data including second environmental data and second physiological data, the second data being generated after the generating the first data, and wherein the control system is further configured to:

based at least in part on the second physiological data, update the representative comfort score associated with the user during the sleep session; and based at least in part on the updated representative comfort score, further adjust the setting of the one or more devices.

10. The system of claim 8, further comprising:

a respiratory therapy device configured to supply pressurized air to an airway of the user by way of a user interface coupled to the respiratory therapy device via a conduit, and wherein the first environmental data includes data generated by one or more sensors of the respiratory therapy device, wherein the control system is further configured to adjust a setting of the respiratory therapy device based at least in part on the determined representative comfort score.

11. The system of claim 8, wherein the one or more sensors includes a microphone, a video camera, an acoustic sensor, a radio frequency (RF) sensor, a photoplethysmogram (PPG) sensor, a piezoelectric sensor, a pressure sensor, a capacitive sensor, a force sensor, a strain gauge sensor, a galvanic sensor, a temperature sensor, a pulse sensor, an oximetry sensor, a LiDAR sensor, an electroencephalography (EEG) sensor, an electromyography (EMG) sensor, an electrooculography (EOG) sensor, an electrodermal sensor, an accelerometer, a light sensor, a humidity sensor, an air quality sensor, or any combination thereof.

12. The system of claim 8, wherein the one or more devices include a thermostat, an air conditioning system, a fan, a heater, a lighting system, a speaker, motorized blinds, a humidification system, a massage system, a vibration system, an adjustable bed frame, an adjustable pillow, an adjustable mattress, a bed temperature regulation system, an adjustable sheet or blanket system, or any combination thereof.

13. The system of claim 8, wherein the one or more devices include a door, curtains, or both.

14. The system of claim 8, wherein the adjust the setting includes adjusting a temperature setting for the environment of the user, a humidity setting for the environment of the user, a luminosity setting for the environment of the user, a humidification setting on a respiratory therapy device, a temperature setting of the respiratory therapy device, a pressure setting of the respiratory therapy device, a volume setting in the environment of the user to mask noise in the environment of the user, or any combination thereof.

15. The system of claim 8, wherein the adjust the setting is further based at least in part on a time of day, a season during a year, demographic data, user inputs, a duration of the sleep session, a point in time during the sleep session, a sleep state of the user, a sleep stage of the user, or any combination thereof.

16. The system of claim 8, wherein the control system is further configured to:

determine a status of wakefulness associated with the user, a status of fatigue associated with the user, health conditions associated with the user, health conditions associated with a bed partner of the user, health conditions associated with a pet of the user, or any combination thereof.

17. The system of claim 8, wherein the first environmental data includes a temperature of the environment of the user, a humidity of the environment of the user, a luminosity of the environment of the user, a noise level in the environment of the user, a noise pattern in the environment of the user, or any combination thereof.

18. The system of claim 8, wherein the first physiological data includes a respiration signal, a respiration rate, a respiration rate variability, an inspiration amplitude, an expiration amplitude, an inspiration-expiration ratio, a number of events per hour, a pattern of events, a duration of each of the events, a heart rate, a heart rate variability, a blood pressure, a blood pressure variability, movement of the user, pain experienced by user, sleep efficiency, therapy efficacy, a core temperature of the user, a sleep stage, apnea-hypopnea index (AHI), a duration of the sleep session that the user is on-therapy, a duration of the sleep session that the user is off-therapy, sleep onset, muscle tone, brain activity, skin conductance, or any combination thereof.

19. The system of claim 8, wherein the setting of the one or more devices is stored in a profile of the user, wherein the adjusted setting of the one or more devices replaces a historical setting of the one or more devices in the profile of the user, and wherein the historical setting of the one or more devices is a default setting selected for the user based at least in part on historical sleep-session data associated with at least one person during one or more historical sleep sessions, the historical sleep-session data including historical physiological data associated with the at least one person and historical environmental data associated with the at least one person.

20. The system of claim 8, wherein values for the first comfort score and the second comfort score are provided on a same scale and obtained from a look up table.

* * * * *